United States Patent
Agnes et al.

(10) Patent No.: US 7,824,920 B2
(45) Date of Patent: Nov. 2, 2010

(54) METHOD OF MASS SPECTROMETRIC ANALYSIS FROM CLOSELY PACKED MICROSPOTS BY THEIR SIMULTANEOUS LASER IRRADIATION

(75) Inventors: George R. Agnes, Coquitlam (CA); Michael J. Bogan, Burnaby (CA)

(73) Assignee: Simon Fraser University, Burnaby, British Columbia (CA)

( * ) Notice: Subject to any disclaimer, the term of this patent is extended or adjusted under 35 U.S.C. 154(b) by 1051 days.

(21) Appl. No.: 10/546,799

(22) PCT Filed: Feb. 24, 2004

(86) PCT No.: PCT/CA2004/000242

§ 371 (c)(1),
(2), (4) Date: Jul. 10, 2006

(87) PCT Pub. No.: WO2004/075208

PCT Pub. Date: Sep. 2, 2004

(65) Prior Publication Data

US 2006/0263899 A1 Nov. 23, 2006

Related U.S. Application Data

(60) Provisional application No. 60/448,898, filed on Feb. 24, 2003.

(51) Int. Cl.
G01N 24/00 (2006.01)
(52) U.S. Cl. .................................. 436/173; 250/282
(58) Field of Classification Search ................. 436/173, 436/618; 250/282
See application file for complete search history.

(56) References Cited

U.S. PATENT DOCUMENTS 5,041,266 A 8/1991 Fox (Continued)

FOREIGN PATENT DOCUMENTS

WO 0235553 A2 5/2002

OTHER PUBLICATIONS

Little et al. "MALDI on a Chip: Analysis of Arrays of Low-Femtomole to Subfemtomole Quantities of Synthetic Oligonucleotides and DNA Diagnostic Products Dispensed by a Piezoelectric Pipet", Anal. Chem. 1997, v. 69, pp. 4540-4546.*

(Continued)

*Primary Examiner*—Yelena G Gakh
(74) *Attorney, Agent, or Firm*—Chernoff, Vilhauer, McClung & Stenzel, LLP

(57) ABSTRACT

This application relates to a process for controllably placing two or more microspots on a target substrate in close proximity to one another. The microspots may then be simultaneously irradiated and the resulting ions detected by mass spectrometry, such as time of flight mass spectrometry. In one embodiment the size and spacing of the microspots on the substrate may be controlled by using an electrodynamic balance during the deposition step. The deposition procedure ensures that at least some of the microspots are spaced-apart on the substrate a distance less than the focused output of a single laser. Simultaneous irradiation of the adjacent microspots may cause desorption plumes of the microspots to interact in a gas phase, such as by ion-molecule reactions. The microspots may be configured to improve the ionization yield of the sample material in the gas phase and/or to increase the frequency of ion-molecule collisions in the gas phase. This allows for desorption of particular classes of compounds to be optimized independently of ionization. Different microspots could include different amounts or types of matrix compounds to enable simultaneously detection of compounds of varied physical and chemical properties within the same sample. One or more of the microspots may include calibrants or other additives for improving detecting accuracy or quantitation. Organized array of closely packed microspots may be created for use as standard reference materials or analyte detectors.

38 Claims, 12 Drawing Sheets

U.S. PATENT DOCUMENTS

| | | | |
|---|---|---|---|
| 6,287,872 | B1 | 9/2001 | Schurenberg |
| 7,157,234 | B2* | 1/2007 | Obremski et al. ............ 435/7.1 |
| 2001/0008615 | A1* | 7/2001 | Little et al. ................. 422/102 |
| 2002/0001853 | A1* | 1/2002 | Obremski et al. ........... 436/518 |
| 2004/0063113 | A1* | 4/2004 | Agnes et al. .................... 435/6 |
| 2008/0203289 | A1* | 8/2008 | Lemaire et al. ............. 250/282 |

OTHER PUBLICATIONS

Sjödahl et al. "Chip with Twin Anchors for Reduced Ion Suppression and Improved Mass Accuracy in MALDI-TOF Mass Spectrometry", Anal. Chem., 2005, v. 77, pp. 827-832.*

Amiri-Eliasi, B., and Fenselau, C., "Characterization of protein biomarkers desorbed by MALDI from whole fungal cells", Anal. Chem., 2001, 73:5228-5231.

Belov, Mikhail E., et al., "Chemical ionization of neutral peptides produced by matrix-assisted laser desorption", Chemical Physics Letters, 1998, 284:412-418.

Berkenkamp, Stefan, et al., "Infrared MALDI mass spectrometry of large nucleic acids", Science, 1998, 281:260-262.

Bogan, Michael J., and Agnes, George R., "MALDI-TOF-MS analysis of droplets prepared in an electrodynamic balance: wall-less sample preparation", Anal. Chem., 2002, 74:489-496.

Bogan, Michael J. and Agnes, George R., "Poly(ethylene glycol) doubly and singly cationized by different alkali metal ions: relative cation affinities and cation-dependent resolution in a quadrupole ion trap mass spectrometer", J. Am. Soc. Mass Spectrom., 2002, 13:177-186.

Bogan, Michael J. and Agnes, George R., "Time-of-flight mass spectrometric analysis of ions produced from adjacent sample spots irradiated simultaneously by a single 337 nm laser", Rapid Commun. Mass Spectrom., 2003, 17:2557-2562.

Brivio, Monica, et al., "Integrated microfluidic system enabling (Bio) chemical reactions with on-line MALDI-TOF mass spectrometry", Anal. Chem., 2002, 74:3972-3976.

Caprioli, Richard M., et al., "Molecular imaging of biological samples: localization of peptides and proteins using MALDI-TOF MS", Analytical Chemistry, 1997, 69(23):4751-4760.

Chaurand, Pierre, et al., "Direction profiling of proteins in biological tissue sections by MALDI mass spectrometry", Anal. Chem., 1999, 71:5263-5270.

Davis, E. James, et al., "The double-ring electrodynamic balance for microparticle characterization", Rev. Sci. Instrum., 1990, 61(4):1281-1288.

Dreiswerd, Klaus, "The desorption process in MALDI", Chem., Rev., 2003, 103:395-425.

Ekstrom, Simon, et al., "Integrated microanalytical technology enabling rapid and automated protein identification", Anal. Chem., 2000, 72:286-293.

Ekstrom, Simon, et al., "Signal amplification using "spot-on-a-chip" technology for the identification of proteins via MALDI-TOF MS", Anal. Chem., 2001, 73:214-219.

Feng, X. and Agnes, George R., "Single isolated droplets with net charge as a source of ions", J. Am. Soc. Mass Spectrom, 2000, 11:393-399.

Feng, Xiao, et al., "Coulomb fission event resolved progeny droplet production from isolated evaporating methanol droplets", Anal. Chem., 2001, 73:4499-4507.

Garden, Rebecca W. and Sweedler, Jonathan V., "Heterogeneity within MALDI samples as revealed by mass spectrometric imaging", Anal. Chem., 2000, 72:30-36.

Gidden, Jennifer, et al., "Gas-phase conformations of synthetic polymers: poly(ethylene glycol), poly(propylene glycol), and poly(tetramethylene glycol)", J. Am. Chem. Soc., 2000, 122:4692-4699.

Gluckman, Matthias, et al., "Mechanisms in MALDI analysis: surface interaction or incorporation of analytes?", Int. J. Mass Spectrom., 2001, 210/211:121-132.

Gobom, Johan, et al., "Alpha-cyano-4-hydroxycinnamic acid affinity sample preparation. A protocol for MALDI-MS peptide analysis in proteomics", Anal. Chem., 2001, 73:434-438.

Guan, Shenheng and Marshall, Alan G., "Equilibrium space charge distribution in a quadrupole ion trap", J. Am. Soc. Mass Spectrom., 1994, 5:64-71.

Hillenkamp, Franz, et al., "Matrix-assisted laser desorption/ionization mass spectrometry of biopolymers", Anal. Chem., 1991, 63(24):1193A-1203A.

Johnson, J.V. and Yost, R.A., "Tandem mass spectrometry for trace analysis", Anal. Chem., 1985, 57:758A-768A.

Karas, M., et al., "Principles and applications of matrix-assisted UV-laser desorption/ionization mass spectrometry", Analytica Chimica Acta, 1990, 241:175-185.

Karas, Michael, et al., "Matrix-assisted laser desorption ionization mass spectrometry", Mass Spectrometry Reviews, 1991, 10(5):335-357.

Karas, M. and Hillenkamp, F., "Laser desorption ionization of proteins with molecular masses exceeding 10 000 daltons", Anal. Chem., 1988, 60:2299-2301.

Keller, Bernd O. and Li, Liang, "Detection of 25,000 molecules of substance P by MALDI-TOF mass spectrometry and investigations into the fundamental limits of detection in MALDI", J. Am. Soc. Mass Spectrom., 2001, 12:1055-1063.

Kinsel, Gary R., et al., "Investigation of the dynamics of matrix-assisted laser desorption/ionization formation using an electrostatic analyzer/time-of-flight mass spectrometer", J. Mass Spectrom., 1999, 34:684-690.

Knochenmuss, Richard and Vertes, Akos, "Time-delayed 2-pulse studies of MALDI matrix ionization mechanisms", J. Phys. Chem. B, 2000, 104:5406-5410.

Knochenmuss, R., et al., "Secondary ion-molecule reactions in matrix-assisted laser desorption/ionization", J. Mass Spectrom., 2000, 35:1237-1245.

Knochenmuss, Richard, "A quantitative model of ultraviolet matrix-assisted laser desorption/ionization including analyte ion generation", Anal. Chem., 2003, 75:2199-2207.

Kruse, Rebecca and Sweedler, Jonathan V., "Spatial profiling invertebrate ganglia using MALDI MS", J. Am. Soc. Mass Spectrom, 2003, 14:752-759.

Leary, James J. and Schmidt, Rebecca L., "Quadrupole mass spectrometers: an intuitive look at the math", Journal of Chemical Education, 1996, 73(12):1142-1144.

Ledford, Edward E., et al., "Space charge effects in fourier transform mass spectrometry. Mass calibration", Anal. Chem., 1984, 56:2744-2748.

Li, Liang, et al., "Analysis of single mammalian cell lysates by mass spectrometry", J. Am. Chem., Soc., 1996, 118:11662-11663.

Little, Daniel P., et al., "MALDI on a chip: analysis of arrays of low-femtomole to subfemtomole quantities of synthetic oligonucleotides and DNA diagnostic products dispensed by a piezoelectric pipet", Anal. Chem., 1997, 69:4540-4546.

Little, Mark W., et al. "Two-laser infrared and ultraviolet matrix-assisted laser desorption/ionization", J. Mass Spectrom, 2003, 38:772-777.

Liu, Jun, et al., "Electrophoresis separation in open microchannels. A method for coupling electrophoresis with MALDI-MS", Anal. Chem., 2001, 73:2147-2151.

Luxembourg, Stefan L., et al., "Effect of local matrix crystal variations in matrix-assisted ionization techniques for mass spectrometry", Anal. Chem., 2003, 75:2333-2341.

Mathurin, J.C., et al., "Investigation of space charge interactions which arise during simultaneous confinement of positive and negative ions in an ion trap mass spectrometry", J. Mass Spectrom., 1997, 32:829-837.

Miliotis, Tasso, et al., "Development of silicon microstructures and thin-film MALDI target plates for automated proteomics sample identifications", J. Neurosci. Meth., 2001, 109:41-46.

Miller, P.E., et al., "The quadrupole mass filter: basic operating concepts", J. Chem. Educ. 1986, 63(7):617-622.

Moskovets, Eugene, et al., "Closely spaced external standard: a universal method of achieving 5 ppm mass accuracy over the entire MALDI plate in axial matrix-assisted laser desorption/ionization time-of-flight mass spectrometry", Rapid Commun. in Mass Spectrom., 2003, 17:2177-2187.

Mowat, Ian, et al., "Enhanced cationization of polymers using delayed ion extraction with matrix-assisted laser desorption/ionization", Rapid Commun. in Mass Spectrom., 1997, 11:89-98.

Murray, Kermit K., "Coupling matrix-assisted laser desorption/ionization to liquid separations", Mass Spectrometry Reviews, 1997, 16:283-299.

Nordhoff, Eckhard, et al., "Sample preparation protocols for MALDI-MS of peptides and oligonucleotides using prestructured sample supports", International Journal of Mass Spectrometry, 2003, 226:163-180.

Onnerfjord, Patrik, et al., "Picoliter sample preparation in MALDI-TOF MS using a micromachined silicon flow-through dispenser", Anal. Chem., 1998, 70:4755-4760.

Onnerfjord, Patrik, et al., "Homogeneous sample preparation for automated high throughput analysis with matrix-assisted laser desorption/ionisation time-of-flight mass spectrometry", Rapid Communications in Mass Spectrometry, 1999, 13:315-322.

Papantonakis, Michael R., et al., "What do matrix-assisted laser desorption/ionization mass spectra reveal about ionization mechanisms?", J. Mass Spectrom., 2002, 37:639-647.

Parks, J. H. and Szoke, A., "Simulation of collisional relaxation of trapped ion clouds in the presence of space charge fields", J. Chem. Phys, 1995, 103(4):1422-1439.

Paul, W., "Electromagnetic traps for charged and neutral particles", Reviews of Modern Physics, 1990, 62:531-540.

Porter, C. J., et al., "The modern mass spectrometer—A complete chemical laboratory", Organic Mass Spectrometry, 1981, 16(3):101-114.

Preisler, J., et al., "Capillary array electrophoresis-MALDI mass spectrometry using a vacuum deposition interface", Anal. Chem., 2002, 74:17-25.

Puretzky, A. A., et al., "Imaging of vapor plumes produced by matrix assisted laser desorption: a plume sharpening effect", Physical Review Letters, 1999, 83(2):444-447.

Rashidzadeh, H., et al., "Matrix effects on selectivities of poly(ethylene glycol)s for alkali metal ion complexation in matrix-assisted laser desorption/ionization", Rapid Communications in Mass Spectrometry, 2000, 14:439-443.

Rejtar, T., et al., "Off-line coupling of high-resolution capillary electrophoresis to MALDI-TOF and TOF/TOF MS", J. Proteome Res., 2002, 1:171-179.

Rubakhin, S.S., et al., "Measuring the peptides in individual organelles with mass spectrometry", Nat. Biotechnol., 2000, 18:172-175.

Schuerenberg, M., et al., "Prestructured MALDI-MS sample supports", Anal. Chem., 2000, 72:3436-3442.

Shevchenko, A., et al., "Charting the proteomes of organisms with unsequenced genomes by MALDI-quadrupole time-of-flight mass spectrometry and Blast homology searching", Anal. Chem., 2001, 73:1917-1926.

Shevchenko, A., et al., "MALDI quadrupole time of flight mass spectrometry: A powerful tool for proteomic research", Anal. Chem., 2000, 72:2132-2141.

Shulman, M. L., et al., "The effects of atmospheric organics on aqueous droplet evaporation", J. Aerosol Sci., 1997, 28 (5):737-752.

Skelton, R., et al., "A MALDI sample preparation method suitable for insoluble polymers", Anal. Chem, 2000, 72:1707-1710.

Smith, James N., et al., "Droplet evaporation and discharge dynamics in electrospray ionization", J. Phys. Chem., 2002, 106:9957-9967.

Taflin, D. C., et al., "Electrified droplet fission and the Rayleigh limit", Langmuir, 1989, 5:376-384.

Tanaka, K., et al., "Protein and polymer analyses up to m/z 100 000 by laser ionization time-of-flight mass spectrometry", Rapid Commun. Mass Spectrom.,1988, 2:151-153.

Vedel, F., et al., "Computation for ions stored in a quadrupole R.F. Trap cooled by a buffer gas. Influence of working conditions on space-charge effects", Int. J. Mass Spectrom and Ion Processes, 1985, 65(1-2):1-22.

Vehring, R., et al., "Electrodynamic trapping and manipulation of particle clouds", Rev. Sci. Instru., 1997, 68:70-78.

Wang, Michael Z., et al., "A solid sample preparation method that reduces signal suppression effects in the MALDI analysis of peptides", Anal. Chem., 2001, 73:625-631.

Wang, B.H., et al., "Gas-phase cationization and protonation of neutrals generated by matrix-assisted laser desorption", J. Am. Soc. Mass Spectrom., 1993, 4:393-398.

Whittal, R. M., et al., "Nanoliter chemistry combined with mass spectrometry for peptide mapping of proteins from single mamalian cell lysates", Anal. Chem., 1998, 70:5344-5347.

Wuerker, R. F., et al., "Electrodynamic containment of charged particles", Journal of Applied Physics, 1959, 30 (3):342-349.

Wyttenbach, T., et al., "Conformations of alkali ion cationized polyethers in the gas phase: polyethylene glycol and bis [(benzo-15-crown-5)-15-ylmethyl] pimelate", Int. J. Mass Spectrom and Ion Processes, 1997, 165/166:377-390.

Zenobi, R., et al., "Ion formation in MALDI mass spectrometry", Mass Spectrom. Rev., 1998, 17:337-366.

Zhang, H., et al., "Capillary electrophoresis combined with matrix-assisted laser desorption/ionization mass spectrometry; continuous sample deposition on a matrix-precoated membrane target", J. Mass Spectrom., 1996, 31: 1039-1046.

Zhang, W., et al., "Radial velocity distribution of molecular ions produced by matrix-assisted laser desorption/ ionization", Int. J. Mass Spectrom. and Ion Processes, 1997, 160:259-267.

Zhigilei, L.V., et al., "A microscopic view of laser ablation", J. Phys. Chem. B, 1998, 102:2845-2853.

Zhigilei, L.V., et al., "Velocity distributions of analyte molecules in matrix-assisted laser desorption from computer simulations", Rapid Commun. Mass Spectrom., 1998, 12:1273-1277.

Zhou, J., et al., "Kinetic energy measurements of molecular ions ejected into an electric field by matrix-assisted laser desorption", Rapid Commun. Mass Spectrom., 1992, 6(11):671-678.

* cited by examiner

METHOD OF MASS SPECTROMETRIC ANALYSIS FROM CLOSELY PACKED MICROSPOTS BY THEIR SIMULTANEOUS LASER IRRADIATION

REFERENCE TO RELATED APPLICATION

This application claims the benefit of U.S. provisional patent application Ser. No. 60/448,898 filed 24 Feb. 2003.

TECHNICAL FIELD

This application relates to a process for controllably placing two or more microspots on a target substrate in close proximity to one another. The microspots may then be irradiated and the resulting ions detected by mass spectrometry, such as time of flight mass spectrometry.

BACKGROUND

MALDI and LDI are methods of producing ions from sample material. The term "MALDI" refers to "matrix assisted laser desorption/ionization". The term "LDI" refers to "laser desorption/ionization". The most common way of detecting the ions produced by these ion sources is by mass spectrometry.[1-3] Thus the ion sources (MALDI and LDI) are commonly integrated with a mass spectrometer (MS). The most common type of mass spectrometer used in this application is a time of flight (TOF) mass spectrometer. Such an ion generation and detection process is therefore sometimes referred to as MALDI-TOF-MS. This process is described in detail in the Applicant's prior international application No. PCT/CA01/01496 filed 23 Oct. 2001 and entitled "Method and Apparatus for Producing a Discrete Particle" (WO 02/035553 A3), the disclosure of which is incorporated herein by reference.

The type of laser most commonly used in MALDI and LDI applications is a $N_2$ laser. The pulsed output of this laser is focused to a spot size on the order of approximately 200 μm in diameter. MALDI produces ions in discrete events, sometimes termed ion packets, because a pulsed laser is used in the MALDI source. Though any mass spectrometer can be used to detect the ions in an ion packet, a TOF-MS detector is best suited to resolving packets of ions as opposed to a continuous stream of ions. The OF instrument accepts a packet of ions and separates those ions based on differences in their masses, which is related to ion velocity differences by $K.E.=0.5\ mv^2$. In a constant DC field, the acceleration of all ions in a population will impart the same kinetic energy into all ions, and thus, because $K.E.=0.5\ mv^2$, a lighter ion will have a higher velocity than a heavier ion. The ions drift, and separate according to their velocities in a field-free tube. The arrival time of the ions at the end of the tube is recorded, and that time is related to the m/z of each ion.

The MALDI source is sometimes referred to in the mass spectrometry literature as a "soft" ionization source. The term "soft" implies that this ion source allows for the detection of intact compounds, even though the compounds are considered fragile (i.e. the compounds easily decompose with the addition of energy). An example of a common MALDI-TOF-MS application is the detection of peptides generated by proteolytic digestion of proteins in a sample, or proteins, oligossacharrides, RNA, DNA and other polymeric materials.[4-7] The MALDI technique may also be effective in analyzing other large biomolecules. One reason that MALDI has become a very successful and widely used technique for preparing gas-phase ions of biomolecules for mass spectrometry is that the preparation of discrete crystallized sample spots is amenable to high-throughput automated analyses.

The MALDI ion source involves the irradiation of a sample using a pulsed laser that causes the desorption/ionization of molecules in the sample spot.[8] Irradiated samples can be in a solid or liquid form, though solid samples are more commonly encountered. A solid sample is prepared by mixing an aliquot of the sample with an aliquot of a matrix solution, then the mixture is delivered (i.e. pipetted) onto a substrate and volatile solvents are allowed to evaporate, leaving behind a solid residue that contains the non-volatile species from the sample plus matrix compound(s). It is believed that the MALDI source results in little fragmentation of the analyte compounds because the technique involves the use of a matrix that is mixed with the sample at a mole ratio of ~1000:1 chromophore:analyte. The matrix is in fact a chromophore that absorbs the output of the pulsed laser used in the MALDI experiment. The matrix absorbs the radiation from the pulsed laser and is itself vaporized and partially decomposed. During the vaporization, analyte molecules are also carried into the gas phase and by either direct ionization or secondary ionization, the analyte molecules become ionized.[9, 10] Direct ionization is the absorption of the laser radiation and ejection of an electron from the analyte. Secondary ionization refers to gas-phase ion-molecule reactions in the plume of material desorbed by the laser. The extent of secondary ionization is not well characterized in the prior art.

The ease with which an analyst prepares a sample for characterization by MALDI is itself easy, simple, and fast: an analyst need only mix the sample with a matrix solution. An aliquot, or all of that mixture is then deposited onto a substrate and the volatile solvent in that mixture is allowed to evaporate dry to leave a dry, solid residue. That residue is then targeted with the laser in the MALDI-TOF-MS instrument. In principle, the preparation of sample material for MALDI-TOF-MS analysis is trivial. In reality, the most frequently encountered problem in the technique is that the sample is simply not detected. There are many reasons for that, such as the threshold level for laser power prior to observing analyte ions. Because of this and other easily and commonly observed characteristics of MALDI, it is widely believed that the detection of an analyte compound in a MALDI experiment critically depends on the crystallization of the analyte compounds with the matrix.

The Applicant's prior international application referred to above (WO 02/035553 A3) describes electrodynamically levitating a sample particle, which may include a solid member, a droplet, a single molecule, or a cluster of molecules, and delivering the particle to a target location. This process is sometimes referred to as "wall-less sample preparation" (WaSP). Briefly, in one embodiment the WASP technology involves the use of an ink-jet droplet generator to create droplets from a starting solution. In order to levitate the droplets in the electrodynamic balance (EDB) a net charge is induced on to the droplet. Though other forms of levitation could be used, each would have their own constraints on the physical and chemical composition of the droplet. The volatile solvents in the starting solution, such as methanol and water, rapidly evaporate (i.e. typically within 1-2 seconds) from the droplet. The evaporation of volatile solvents concentrates the non-volatile (plus low volatility) solutes that were in the starting solution inside what is now descriptively referred to as the levitated droplet residue. That droplet residue is then deposited onto a target substrate. Translating the substrate relative to the EDB, or vice versa, and repeating the process of creating and levitating a droplet followed by the deposition of that residue allows a user of WaSP to pattern multiple spots of materials onto a substrate.

As described herein, smaller spots of sample may prepared by adjustment of the time invariant (i.e. DC) and time variant (i.e. AC) electrical potentials applied to the EDB. Since the EDB is in effect an atmospheric pressure or "Paul trap", one can describe droplet/particle stable levitation in a-q space. The term "Paul trap" is in reference to the contributions made by Wolfgang Paul which led to his being awarded a (Physics) Nobel prize.[11]

Alternatively, a user of WASP could employ the use of droplets that are themselves not stable. Specifically, it is possible to allow the levitated droplet to become electrically unstable by adjustment of the starting solution composition, induction potential, or the environmental conditions within the levitation chamber. If a droplet with net charge becomes unstable, it can undergo one or more Coulomb explosion events.[12] If so, the material ejected from the droplet can be directed onto different regions of a target substrate by introducing an electric field orthogonal to the direction for deposition of the levitated droplet onto a substrate.

Moskovets et al. have shown that by placing two discrete sample traces within 100 µm to 4 mm of one another, and performing MALDI on them separately, mass detection accuracy gains were achieved for traces in the center and edge of their MALDI target plate [13]. Moskovets et al. do not teach the advantages of irradiating two or more closely spaced samples simultaneously.

Other sample preparation methodologies are known in the prior art. The Karger group has developed, and patented, the use of a vacuum deposition of the liquid emerging from a capillary electrophoresis (CE) column.[14, 15] The purpose of the vacuum is to remove volatile solvent quickly to reduce the extent to which sample smears on the plate. The utility of this technology has been demonstrated by the Karger group to enable the deposition of materials as tracks (i.e. eluant from a separation) alongside another track of material, such as an internal standard. In their work, the substrate was moved underneath the laser spot (i.e. rastered), effectively sampling both tracks of materials serially, but not simultaneously, between the two tracks of materials. The objective of their work described in this manuscript was on improving mass accuracy of the compounds detected in a MALDI-TOF-MS experiment.

The Li group has developed a nanoliter sample preparation platform to the extent that they now refer to the technology as a nanoliter chemistry station.[16, 17]

Smith has described the use of open channel electrophoresis for coupling separations to MALDI-TOF-MS.[18] Along the same lines, a microfluidic sample preparation system has also been developed for preparing sample material for MALDI-TOF-MS.[19] Several other groups are preparing spots of sample materials using droplet dispensers with direct deposition onto a substrate.[20-24]

Early applications of MALDI time of flight mass spectrometry (TOFMS) in the study of biomolecules using an organic matrix used sample spot sizes (~5 mm$^2$) that were much larger than the laser spot diameter (~$10^{-3}$ mm$^2$) used for analysis. [25-27] Since then, this approach has been almost universally accepted because, by irradiating a single sample spot that was larger than the laser diameter, one could ensure that only the sample of interest was being probed and sample preparation using micropipettes was trivial. [28-32] However, as experienced by most practitioners of MALDI, even though only a single sample spot is analyzed the large sample spot does not produce uniform signals over its entire area because of microheterogeneity in the sample.[33,34] This has led to the notion of 'hot' or 'sweet' spots, small regions within a large sample spot from which large fluxes of analyte ions are detected. One of the responses to this problem has been to devise new methods that create smaller sample spots that reduce the need to search for hot spots because almost the entire sample is irradiated.[35-41] These approaches have also fulfilled demands for less sample consumption and the preparation of higher densities of sample spots on a single MALDI plate to increase throughput. For example, 100×100 to 400×400 µm microfabricated silicon picoliter vials that hold sample dispensed through a piezoelectric droplet generator have been shown to increase sensitivities 10-50 times relative to dried-droplet preparation. [39] Note that the laser spot diameter used to analyze the samples deposited in the picoliter vials was ~100 µm in diameter and thus it and the sample spots were nearly the same size. Similarly, the development of a microspot sample preparation technique using a picoliter syringe demonstrated that as little as 20 pL of sample volume could be manipulated to create sample spots of ~100 µm in diameter, enabling the analysis of the contents of a single red blood cell (~87 fL volume).[42] The laser spot size that was used for analysis was in the shape of an oval, 50×180 µm, so again the sample spot and laser spot size were nearly equal.

Another advantage of small sample spot sizes, high sensitivity, was clearly demonstrated by the detection of 42 zeptomoles (25 000 molecules) of substance P from a 0.08 mm diameter microspot.[43] That study also revealed that the minimum absolute detection limit was set by the number of molecules per µm$^2$ (>5 molecules). This suggests that if the sample spot size can be decreased while maintaining the required analyte density, very high density sample spot arrays can be produced on MALDI plates for high-throughput analyses at high sensitivities while consuming very small volumes of sample. Recent applications of high-density sample spot preparations include the coupling of separations techniques such as liquid chromatography and capillary electrophoresis to MALDI for analysis by offline mass spectrometry[28,44-46] and the spotting of matrix onto a sample for subsequent imaging of the ions on the surface by mass spectrometry.[47-50] As with many other disciplines, there are clear advantages for MALDI sample preparation to move towards smaller and smaller dimensions.

While other sample preparations methodologies useful for MALDI-TOF-MS are known in the prior art, improved methods for controllably depositing microspots of sample material on a target substrate in close proximity to one another are desirable as are improved methods for simultaneously irradiating adjacent microspots.

SUMMARY OF INVENTION

In accordance with the invention a method of analyzing a sample material is described. The method comprises the steps of controllably depositing two or more discrete microspots on a substrate in close proximity to one another, wherein at least one of the microspots comprises the sample material, and irradiating the microspots simultaneously.

The irradiation may be implemented by directing single or multiple laser shots to the microspots. In one embodiment the irradiation causes the desorption plumes of the microspots to interact in a gas phase. For example, the interaction between the plumes may be an ion-molecule reaction. The method may include the step of detecting secondary ionization in the gas phase. The ions produced by the ionization process may be detected in a mass spectrometer, such as a time of flight mass spectrometry.

In one embodiment the microspots are deposited on the substrate in a predetermined array or pattern. The deposition step may involve moving the sample material from an electrodynamic balance to the substrate. For example, the microspots may be controllably deposited on the substrate by sequentially removing charged particles from said electrodynamic balance, wherein the charged particles are deposited on the substrate in an array corresponding to the mass-to-charge ratios of the particles. Alternatively or additionally the deposition may comprise forming the microspots on the substrate using a micropipette or an ink-jet droplet generator.

The diameter of each of said microspots is preferably within the range of approximately 1 to approximately 200 µm and more preferably less than about 100 µm. The microspots are deposited in close proximity to one another such that the distance between at least two of the microspots is less than the focused output of a single laser. For example, such distance may be less than about 200 µm.

At least one of the microspots may include a calibrant having a known mass. The calibrant may be in the same microspot as the sample material and/or in a separate microspot closely spaced to the sample material.

The invention further comprises depositing a plurality of the microspots in close proximity in a test region of the substrate, wherein a first one of the microspots comprises the sample material mixed with a first amount of matrix material and a second one of the microspots comprises the sample material mixed with a second amount of the matrix material, wherein the first and second amounts differ. Similarly, a first one of the microspots may comprise the sample material mixed with a first matrix material and a second one of the microspots may comprise the sample material mixed with a second matrix material, wherein the first and second matrix materials differ. At least one of the first and second matrix materials may comprise a mixture of different matrices. The test region is smaller in size than the focused output of a single laser such that at least the first and second ones of the microspots are irradiated simultaneously.

In one embodiment at least some of the microspots deposited within the test region comprise materials selected to improve the ionization yield of the sample material in the gas phase and/or to increase the frequency of ion-molecule collisions in the gas phase. By selecting the composition of the microspot containing the sample material, and adjacent microspots in close proximity to the sample material which may be irradiated simultaneously, the desorption and ionization steps may be effectively decoupled and optimized.

The sample material may comprise an analyte in the form of a solid member, a droplet, a single molecule or a cluster of molecules. For example, the sample material may be a biomolecule. In other embodiments the sample material may be a mixture of different types of compounds.

In one embodiment, the invention may comprise depositing an array of microspots of known composition on the substrate, wherein the microspots may comprise different sample materials. The different sample materials deposited could have known compositions and the substrate having the array of microspots formed thereon could be used for instrument testing or sample identification/characterization purposes. In one example, the substrate may include a test region having a test material and the microspots could be deposited in the test region. At least some of the microspots may comprise sample material potentially reactive with the test material. For example, the microspots may comprise one or more known reagents potentially reactive with the test material. In one embodiment of the invention a method of controllably depositing a sample material is provided which includes the steps of providing a target substrate having a test region, wherein a test material is at least partially applied to the substrate in the test region; controllably depositing two or more discrete microspots on the substrate in the test region in close proximity to one another, wherein at least one of said microspots comprises the sample material; and detecting any reactivity between said test material and the sample material in the test region.

The test region of the substrate may have at least one microfabricated pattern formed therein. The microfabricated pattern may be adapted for holding materials such as reagents, calibrants, solvents, gas phase ionization yield enchancers, and sample material.

BRIEF DESCRIPTION OF DRAWINGS

In drawings which illustrate embodiments of the invention, but which should not be construed as restricting the spirit or scope of the invention in any way.

FIG. 6A shows the mass spectrum of a single microspot containing CsCl. FIG. 6B shows the mass spectrum of a microspot formed by depositing a droplet containing CsCl on top of a droplet containing PEG1000. FIG. 6C shown the mass spectrum of a CsCl microspot and a PEG1000 microspot, both contained within the laser diameter, where the center-to-center droplet spacing was ~115 μm. FIG. 6D shows the mass spectrum of a CsCl microspot and a PEG1000 microspot, both contained within the laser diameter, where the center-to-center droplet spacing was ~84 μm. Ions marked by an asterisk denote sodiated PEG and those marked by a circle denote cesiated PEG. The sodiated and/or cesiated PEG1000 with 21 ethylene oxide units (EO21) has been labeled in each spectrum for orientation. Each spectrum was normalized to the Cs+ ion intensity.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

This application relates to formation of closely packed, discrete microspots on a substrate and irradiation of the microspots with a laser to produce ions. The ions may be detected in a mass spectrometer, such as a time of flight mass spectrometer. If the substrate is a MALDI plate, the invention may be used to improve the performance of MALDI-TOF-MS. As described below, the distance between at least some of the deposited microspots is less than the focused output from a laser to ensure that such microspots are irradiated simultaneously. The invention enables improved application of existing, or, the introduction of new analytical methodologies.

By way of introduction, FIGS. 1A-1D compare four hypothetical MALDI-TOF mass spectra that would be obtained when discrete sample spots 10 of different diameters and center-to-center separations, each containing a single analyte (i.e. a sample material), were deposited on a substrate 12, such as a MALDI plate, and irradiated using a fixed laser spot size. In reality, the effective irradiation area of an $N_2$ laser 14 in a UV-MALDI ion source varies from instrument to instrument so, for the purposes of this discussion, the term fixed laser spot size refers to the area irradiated by a laser 14 from a single instrument using identical energy settings.

Figure 1A:
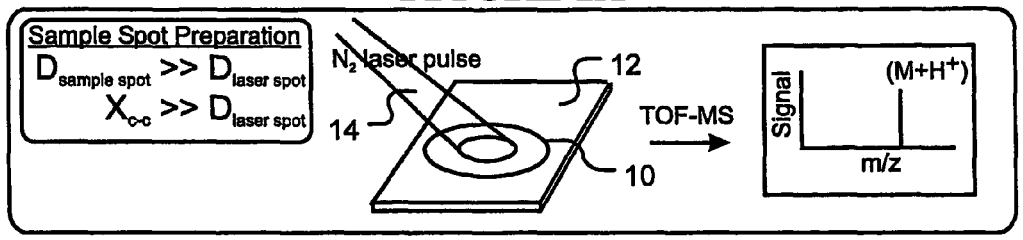
FIG. 1A-1D are hypothetical mass spectra of ions that would be detected from MALDI sample spots, each containing a single analyte (M, N, O, P, . . . ), prepared with different diameters ($D_{sample\ spot}$) and center-to-center separations ($X_{c-c}$), but analyzed using a constant laser spot size ($D_{laser\ spot}$).
Figure 1B:
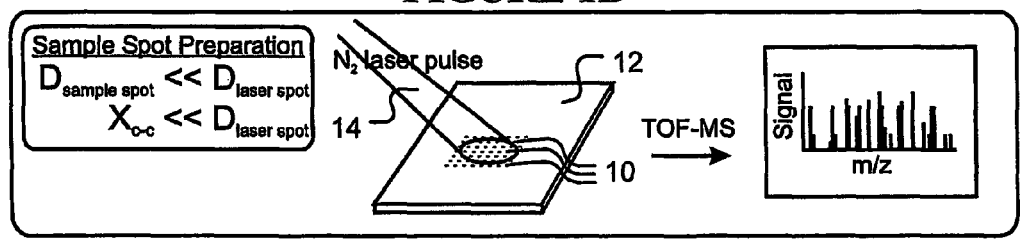
Figure 1C:
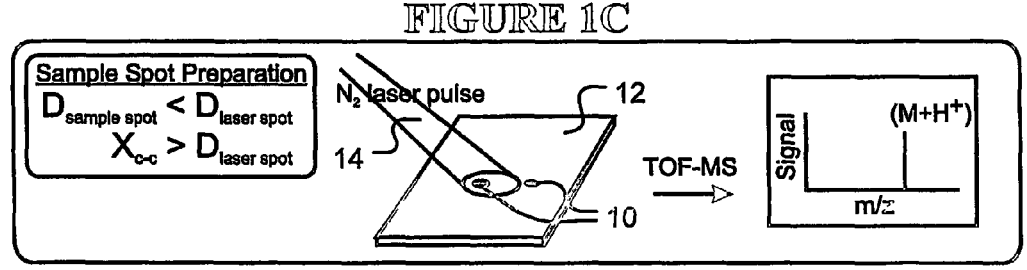
Figure 1D:
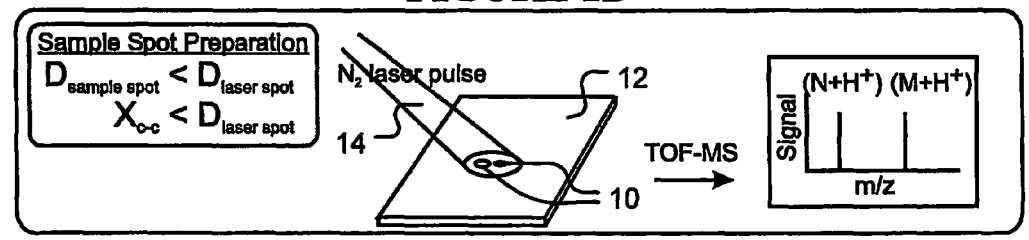

The first set of conditions described are those utilized in the majority of MALDI sample spot preparations, a very large sample spot 10 relative to the laser spot size used to analyze it (FIG. 1A). For example, a single well from a typical 100-well plate has a diameter of 2 mm whereas the laser spot size is typically an oval ~200×~100 μm. FIG. 1B illustrates the opposite extreme, very small sample spots 10 (i.e. microspots) relative to the laser spot size that are very densely packed. For example, if 20 μm diameter sample spots were created in a two-dimensional array with center-to-center separations of 30 μm., ~1.1×10$^5$ spots would only fill 1 cm$^2$. Such a sample spot array would be of higher density than what could be actually analyzed on a single spot basis unless the laser spot size was reduced to <30 μm. in diameter. Assuming a laser diameter of 200 μm, ~40 discrete sample spots 10 would be irradiated in a single laser shot, resulting in an extremely complex mass spectrum (FIG. 1B). These criteria set the density with which single sample spots 10, prepared for discrete analysis, can be packed. Therefore, when the sample spot size is decreased to near equal or below the laser spot size, the center-to-center separation between adjacent sample spots 10 must be greater than the diameter of the laser spot to ensure that only a single sample spot is irradiated (FIG. 1C). This is the approach that is presently applied in the prior art to high-density sample spot preparations where the sample spot size is on the same order of magnitude as the laser spot diameter because it generates a mass spectrum derived from a single sample spot 10.[35]

If only a small number of sample spots 10 can fit within the laser spot size, each laser shot will simultaneously irradiate several sample spots 10 (i.e. microspots), yet the complexity of the spectrum remains manageable. For example, in FIG. 1D there are only two sample spots 10 from which ions will be produced and, because each sample spot 10 contains a single analyte, there would be only two signals in the mass spectrum. Therefore, by carefully selecting the composition of each sample spot 10, the complexity of the mass spectrum can be controlled. The advantage of this approach is that analysis of multiple sample spots 10 can be performed simultaneously, dramatically impacting throughput. It is important to note that portions of two adjacent sample spots 10 that are large relative to the laser spot size (diameters >200 μm) can also be irradiated simultaneously by a single laser pulse if their edges approach each other within the laser spot size. The inventors have employed this scenario to characterize ions created by simultaneously irradiating adjacent sample spots 10. This approach provides the opportunity for multiplexed sample analysis. In one embodiment each sample spot may be on the order of 10-50 micrometers in cross-section.

One advantage of the present invention is that each of the sample spots 10 (sometimes referred to herein as microspots) which are irradiated simultaneously may not necessarily contain sample material. Each microspot may comprise a quantity of a single material or a mixture of different materials, such as droplets, particles, or combinations thereof. Some microspots may include calibrants of known mass to improve detection specificity. Calibrants may be present either in the same microspot as the sample material or in a different microspot, or both. It is well recognized that internal mass calibration (i.e. in spectrum) improves the mass accuracy by a factor of 10 or more as compared to external mass calibration. One of the factors that leads to this increase mass accuracy is that the ions produced by the process originate from the same position on the target substrate 12. This is important since imperfections in the flatness of the substrate's surface, or flatness in the surface of the sample, can change the time of flight of identical ions produced from two different positions on the target substrate. Further, by adding internal mass calibrant as a separate spot, the calibrant will not suppress the ion abundance of the compounds in the sample.

MALDI experiments typically suffer from poor shot-to-shot reproducibility. However, it has been shown that is the use of a compound as an internal standard for signal intensity variations between laser shots (i.e. the ion signal intensity of the analyte is divided by the ion signal intensity of the internal standard) offers a convenient method to achieve improved quantitative performance in a MALDI-TOF-MS experiment. The internal standard could be, for example, a known peptide or a pharmaceutical compound, a metabolite, or a strand of single or duplex DNA. Alternatively, the internal standard could be a protein (or one of its peptides) isolated from the control in a proteomics experiment wherein the sample would be the corresponding peptide, but labeled with, for example, a heavy-atom. Such a strategy is commonly used in liquid chromatography-electrospray-mass spectrometry proteomics experiments.

Analyte signal intensity suppression is observed in MALDI experiments when an inappropriate quantity of internal standard is mixed with the sample. The present invention is of further benefit because, by having the internal standard isolated from the sample in physically separate spots, signal suppression of low abundance compounds by high abundance compounds can be avoided.

Multiple spotting of chemical degradation reagents onto a pre-existing 'large' spot of sample material can be useful for performing reactions that will improve identification of the sample material without requiring additional consumption of the sample. Analysis using this application would provide the user with immediate access to the original sample as well as the modified sample, for comparison. This application could use any existing or developed reaction chemistry involving the modification of existing MALDI sample spots. One example of such a method could be to apply different enzymes or reagents capable of, for example, proteolysis selective removal of post-translational modifications on a protein, such as oligosaccharrides or phosphates, or more generally a chemical reaction.

Microspots may include additives to enhance ionization yields and/or to enhance ion-molecule reactions in the gas phase. Thus the desorption and ionization steps may effectively be decoupled to optimize both process depending on the nature of the sample material and other parameters. For example, the sample could be prepared in such a manner as to enable optimization of the desorption of the sample compounds, and that spot of sample would be surrounded by spots of different materials that are designed to improve gas-phase ionization yield. This approach physically decouples the desorption from the ionization in a MALDI experiment. This methodology could provide lower detection limits for all compounds analyzed by MALDI because, at present, a very high percentage of analyte is desorbed from sample spots as neutral compounds. In addition, this method has potential to reduce detection limits for compounds that are presently difficult or undetectable by MALDI. An example of difficult to detect compounds includes DNA and RNA that are ~>100 bases.

An example application of this technology is to detect high mass proteins with higher sensitivity. In addition to the issues associated with the detection of high mass-to-charge entities by conventional ion detectors used in mass spectrometers, it is possible that the current low sensitivity for these compounds is based on their kinetic energies within the desorption plume. High mass proteins 'fly' relatively slowly away from the substrate following a laser shot. By the time the protein compounds are in the extraction region for the mass analyzer, the small molecules and ions that could have collided with them and protonated the protein compounds through ion-molecule reactions have long since left the extraction region because their velocities were much greater than the protein compounds. Close packing of materials in microspots around a protein-compound containing spot could be performed where the compositions of the closely packed materials will have been designed and optimized to provide high yields for gas phase proton transfer by ion-molecule collisions. A single laser shot, or multiple laser shots will be used in a sequence whose duration is several nanoseconds, to increase the yield of gas phase analyte ions with this basic strategy for close-packing of sample spots. The mechanism for increasing analyte ion yields that is exploited could be effecting an increased frequency of ion-molecule collisions and/or by increasing the yield for proton-transfer to the analyte.

As indicated above, the present invention may be employed to closely pack multiple microspots of a single sample where, within each spot, the sample was mixed and co-precipitated with different matrices or different combinations of matrices. This application is presently applied with conventionally prepared sample spots to increase the peptide coverage observed from the digestion of a protein in a proteomics experiments because it is known that certain peptides have higher desorption efficiencies with certain matrices. The benefit of the close packing of microspot approach, coupled with simultaneous irradiation, is that the samples could be analyzed all simultaneously, increasing throughput and decreasing the time required to perform the analysis.

Although the invention is described herein principally in the context of MALDI-TOF-MS, arrays or patterns of closely packed microspots could be used as constructs for other applications or instrumental techniques. For example, microspot arrays comprised of known sample materials deposited in a known configuration could be used as reference materials for calibrating molecular imaging instruments. In one embodiment microspot arrays could be employed for detecting or characterizing a test material (either within one or more microspots or applied to the target substrate).

The following examples will illustrate the invention in further greater detail although it will be appreciated that the invention is not limited to the specific examples.

EXAMPLE 1

Chemicals

Reagent grade methanol, glycerol, cesium chloride, and sodium chloride were purchased from BDH. Poly(ethylene glycol) of average molecular weight 1000 amu (PEG1000) and the MALDI matrix α-cyano-4-hydroxy cinnamic acid (HCCA) were purchased from Sigma. The droplets used to characterize particle levitation and ejection from the EDB were created from starting solutions consisting of methanol plus 1-8% glycerol. The NaCl particles were prepared using a starting solution comprising 3 M NaCl in water. The solution used to create the microspots containing PEG1000 consisted of $1.0 \times 10^{-3}$ M PEG1000 and $5.0 \times 10^{-5}$ M HCCA in a methanol solution containing 4% glycerol. Likewise the microspots containing CsCl were made from a solution consisting of $1.0 \times 10^{-2}$ M CsCl and $5.0 \times 10^{-5}$ M HCCA in a methanol solution containing 4% glycerol.

Electrodynamic Balance

Figure 1E:
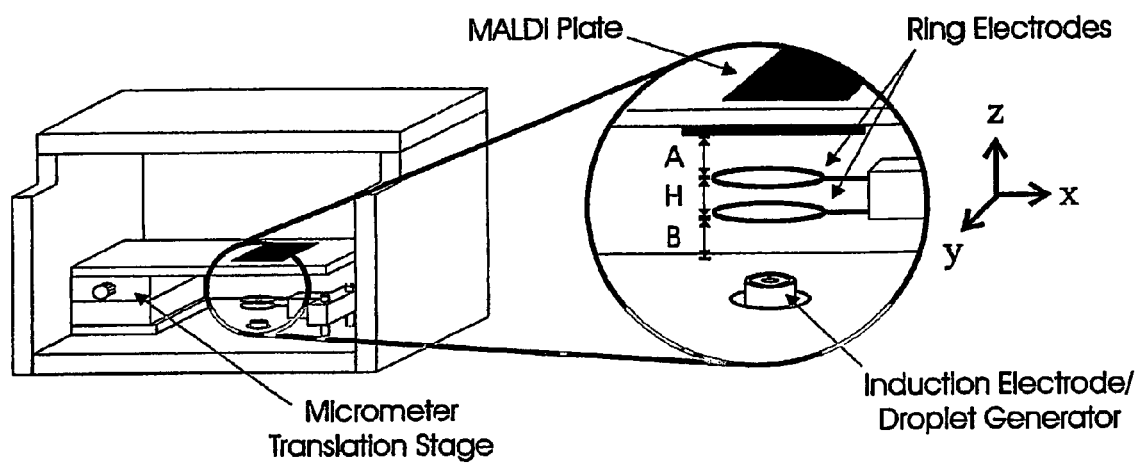
FIG. 1E is a schematic view of a levitation chamber. The separation between the each electrode is indicated as A=H=B=6 mm. The micrometer translation stage moves the MALDI plate along the y-axis.

The droplet generator, the ring electrodes of the EDB, and the MALDI sample plate were enclosed in a plexiglass chamber to eliminate air convection in the laboratory from disturbing the trajectories of levitated objects (FIG. 1E). The EDB was constructed using copper wire (0.9 mm in diameter) that was shaped into 2 cm diameter rings mounted parallel at a separation distance of 6 mm. [51] No DC potential was applied directly across the EDB ring electrodes. The vertical positions of droplets/particles in the EDB were manipulated by the DC potentials applied to the induction electrode and the top plate, which served also as the target plate (MALDI plate) for particle deposition. The amplitude of the AC potential (60 Hz) applied to the ring electrodes (in phase) ranged from 0 to 2,700 $V_{0-P}$. Particles or droplets in the EDB were illuminated via forward scattering by a 4 mW green HeNe laser.

The DC potential applied to the MALDI plate caused the ejection of particles from the EDB to be along the z-axis at x, y=0. The MALDI plate was mounted on a translation stage whose position relative to the EDB was changed between each particle deposition event to create an array. The details of extracting a single levitated particle from the EDB and depositing it onto a plate are reported in the results section. Images of levitated particles or microspot arrays were collected by focusing a digital camera through a microscope objective to the center the ring electrodes or onto the MALDI plate.

Droplet Generation

The droplet-on-demand generator (Uni-photon Systems, model 201, Brooklyn, N.Y.) was fitted with an in-house constructed nozzle (40 μm diameter).[52] The tubing of this generator was filled with a starting solution and then the droplet generator assembly was mounted inside the levitation chamber (FIG. 1E).

The volume of the initial droplet formed from this generator can be controlled through variation of the DC amplitude applied to the piezoelectric strips of the droplet generator, use of a different sized nozzle, or changing the composition of the starting solution. We have found it most practical to vary the concentration of dissolved solids or the amount of non-volatile solvent in the starting solution to vary the mass of non-volatile material in the levitated particle. The volatile solvent in the starting-solution evaporated within a few seconds following the droplet formation event [52, 53] to leave behind a residual droplet or particle.

During the formation of the droplet, an induction electrode positioned 5 mm above the droplet generator's nozzle imparted an image charge onto the forming droplet. Thus the net charge carried by each droplet was of opposite polarity relative to the induction electrode. The induction electrode potential was set between 0-250 V, positive or negative. These factors were used to vary the magnitude of the mass-to-charge (m/z) ratio of the levitated particles.

Offline Microspot MALDI-TOF Mass Spectrometry

All mass spectra were collected after removing the target plate from the droplet levitation chamber and inserting it into a Perseptive Biosystems Voyager-DE MALDI-TOF-MS (Framingham, Mass., USA). Mass spectra of adjacent microspots were obtained by centering the focus of the laser between the two microspots such that both were contained within the ~200 μm diameter of the $N_2$ laser. All spectra were collected with a 100 ns delayed extraction time to allow sufficient time for desorption plumes to interact.

Microspot Array Formation from a Population of Levitated Particles

Balance and Deposition Potential vs. AC Trapping Potential

Figure 2:
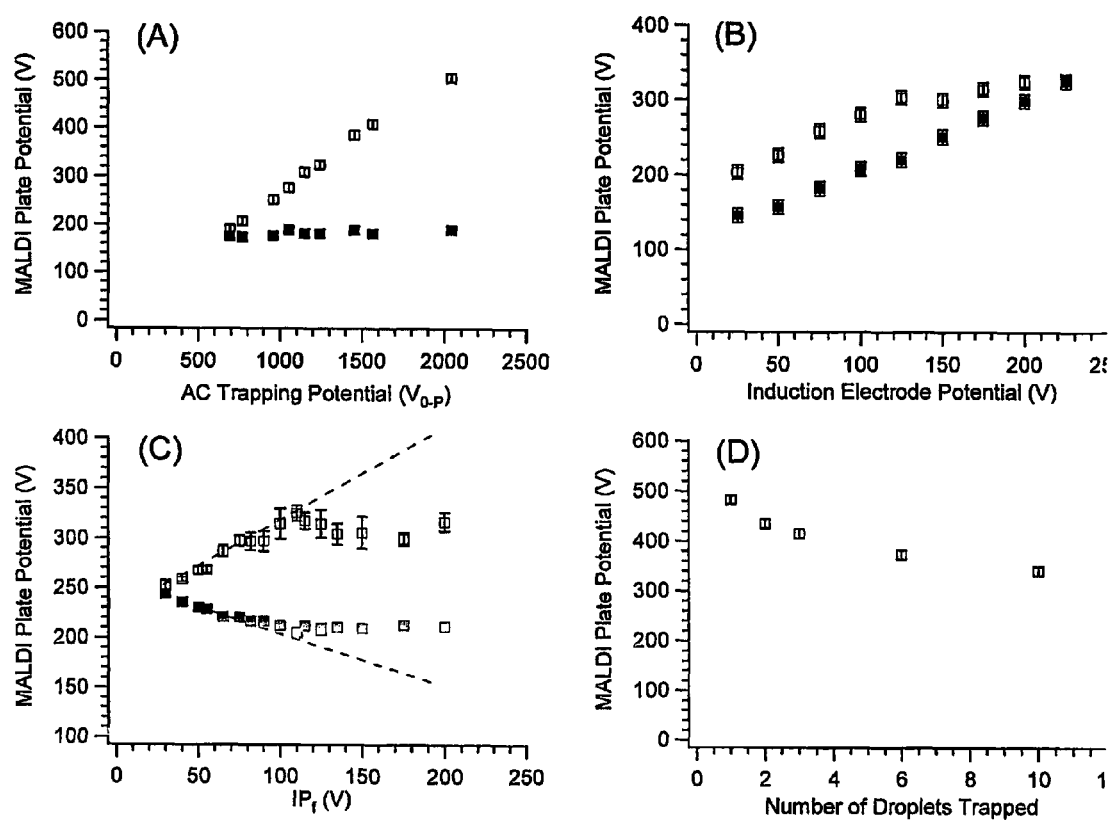
FIG. 2A-2D are graphs showing a DC potential applied to the MALDI sample plate required to balance a single droplet at the null point (BP, filled squares), and to eject the same droplet from the EDB at its deposition potential (DP, open squares) as a function of (2A) the AC trapping potential applied to the EDB rings with $IP_f$ fixed at 75 V, (2B) the DC potential applied to the induction electrode at a fixed AC potential of 960 $V_{0-P}$ and $IP_f$ fixed at 100 V, and (2C) the $IP_f$ applied during droplet formation. Lastly, (2D) the DP of the first droplet from a population of n similarly created droplets levitated in the EDB as a function of n was plotted. Each data point is the average of seven or more droplets created under the same conditions.

In this set of experiments, a single negatively charged droplet was formed at an induction potential ($IP_f$) of 75 V and the target plate potential held at 0 V. The amplitude of the AC trapping waveform was varied (FIG. 2A). The balance potential (BP) was measured by increasing the DC potential applied to the target plate until the droplet was focused as a single spot in the center of the balance (the null point). The deposition potential (DP) was defined as the voltage applied to the target plate necessary to remove a droplet from the EDB, because once removed from the EDB, the particle was deposited on the target plate.

The data plotted in FIG. 2A show that the DP of a droplet increased with increased AC amplitude, because the magnitude of the electric field acting to restore the droplet at the center of the EDB increased. This data concurs with the observation by Wuerker et al. that a particle array can be compressed towards the null point by increasing the amplitude of the AC trapping potential. [54] However, the BP was independent of trapping potential because only the DC potentials were used to offset the force of gravity. FIG. 2A has plotted in it the data for a single $IP_f$, but droplets produced at $IP_f$=25, 50, 100, 125, 150, 175, 200, and 225 V each produced similar trends for BP and DP.

Deposition/Balance Potential vs. Induction Electrode Potential (IP)

A droplet created with $IP_f$=100 V was trapped and levitated using an AC potential of 960 $V_{0-P}$. The potential of the induction electrode was then adjusted to a value between 25-200 V. The BP and DP were then measured for the droplet. Data for replicate experiments are plotted in FIG. 2B. Both DP and BP increased as the induction electrode's potential became increasingly positive with a constant AC trapping potential because the droplet, carrying net charge of opposite polarity, experienced a greater attractive force toward the induction electrode. The DP and BP converged at IP>150 V because the levitated droplet's m/z likely placed it near the edge of the a-q stability region. [55-57]

Deposition/Balance Potential vs. Induction Potential During Droplet Formation (IPf)

Here a single droplet was created using an $IP_f$ between 25 and 200 V, and levitated with an AC trapping potential of 1150 $V_{0-P}$. With that single droplet levitated in the EDB, the potential of the induction electrode was set to 100 V and the BP and the DP were measured. The data plotted in FIG. 2C shows that BP initially decreases and DP initially increases with increased $IP_f$. All of the droplets used to collect the data plotted in FIG. 2C were created with identical amplitudes applied to the piezoelectric crystal in the droplet generator, and thus it can be assumed that they each had the same nominal mass. Therefore, as the $IP_f$ increased, the m/z of the droplet decreased. Within the range of droplet m/z examined with this data set, the droplets with lower m/z (higher mobility) [58] experienced a stronger restoring force at any given fixed AC trapping potential, and thus a deeper trapping potential well depth. Thus as $IP_f$ increased, it became easier to balance the droplet at lower BP, yet more difficult to eject it from the EDB.

The dashed lines in FIG. 2C depict the BP and DP trends before $IP_f$=100 V. The lines are not linear fits and serve only as a guide for the eye. Extrapolating these lines to $IP_f$>100 V indicates deviation of the BP from the dashed line, and an increase in its standard deviation. A droplet can only carry a certain amount of net elementary charge before it exceeds the Coloumb fission limit, the point when the electrostatic repulsion due to the net charge on the surface of the droplet equals the surface tension. [59] In a droplet that is shrinking in size due to evaporation, exceeding the Coulomb fission limit causes the droplet to rupture to yield numerous small droplets termed progeny that are enriched in net charge and one, or possibly several residual droplets, that contain the remaining net charge and mass. [60] All of the droplets following the first Coulomb fission are categorized as secondary. We have previously characterized similar droplets generated at $IP_f$=125V undergoing Coulomb fission using laser light scattering. [60] We believe the deviation observed in FIG. 2C at $IP_f$>100 V was caused by droplets undergoing Coulomb fission and the data for BP and DP was acquired for the largest secondary droplet For $IP_f$ beyond the threshold of ~100 V, the erratic behavior in the BP and DP can be attributed to variability in the amount of charge ejected from the methanol/glycerol droplets, and possibly the additional factor that the secondary droplet was closer to the edge of the a-q stability region. [55] Thus, to achieve reproducible behavior when depositing droplets into a microspot array, and to not lose dissolved solids, the $IP_f$ should remain as low as possible.

Deposition Potential vs. Number of Droplets Trapped

The DP required to deposit the first droplet from a population of n droplets decreased as n increased (FIG. 2D). All droplets were created with $IP_f$=100 V and each had the same nominal m/z. The electrostatic repulsion between droplets in the EDB introduces space charge. [58, 61-66] This perturbation of the trapping potential well depth of the levitated droplets increases in severity as the number of droplets levitated increases, as indicated by the data plotted in FIG. 2D. With the ejection of a droplet from the EDB, the repulsive force experienced by the remaining levitated droplets decreased, thus necessitating higher DP to eject the next droplet from the EDB.

Microspot Arrays

Figure 3:
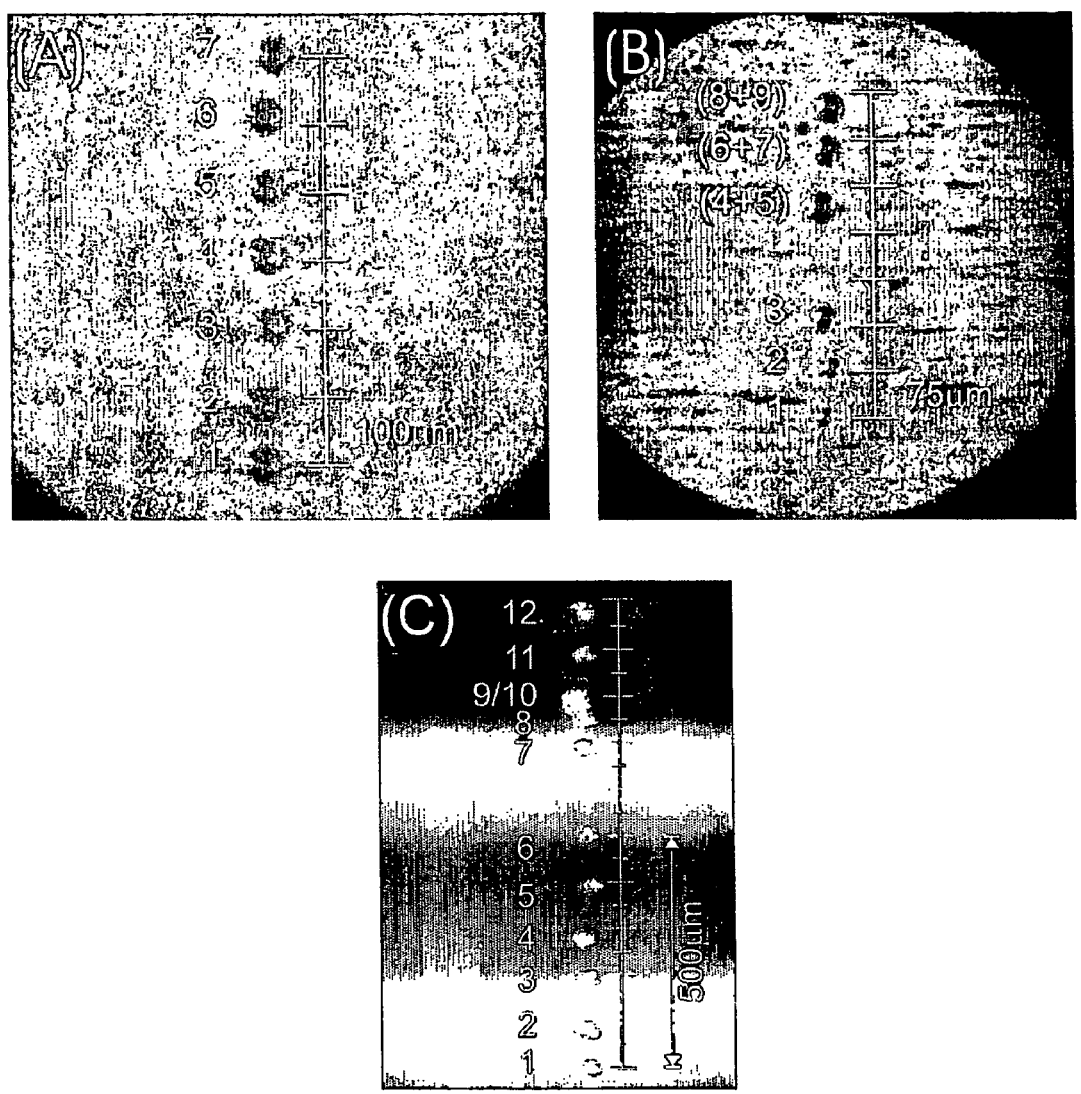
FIG. 3A is a magnified digital image from an optical microcope showing seven droplets created from a methanol solution containing 8% glycerol deposited onto a target plate with 100 µm center-to-center spacing.
FIG. 3B is a magnified digital image showing an array of six deposited droplets created from nine droplets levitated in the EDB.
FIG. 3C is a magnified digital image showing an array of three particles of NaCl deposited from the EDB.

Single droplet ejection from the EDB coupled with micrometer translation of the MALDI sample plate was utilized to create arrays of deposited droplets or particles. FIG. 3A shows an array of deposited droplets 25 µm in radius. The starting solution used to create these droplets contained 8% by volume glycerol in methanol, and the radius of the levitated droplet was an estimated 17 µm. This array was created from a population of seven droplets levitated in the EDB, where after each droplet was deposited the translation stage was moved 100 µm relative to the EDB.

Higher density arrays can be formed by using starting solutions that contain lower concentrations of the non-volatile solvent, glycerol. FIG. 3B shows an array formed using nine droplets created from a starting solution that contained 2.8% glycerol in methanol. The image of this array demonstrates the flexibility in both the number of droplets deposited at any one position and the spacing between the site of deposition. The first three droplets were deposited individually at a center-to-center separation distance of 75 µm. Droplets 4-9 were deposited with two droplets per deposition position, and the spacing between those sites was 75 µm. The deposition of two glycerol droplets per site was used to create the three larger deposited droplets in the upper half of FIG. 4B, the first of which was 150 µm above the last of the three sites of droplet deposition where only a single droplet was deposited per site. The average radius of the deposited sample material spot that was formed using two single droplets was 50 µm, whereas the sample material spot size formed using a single droplet was 35 µm. A factor that was likely limiting the spatial accuracy of the object deposition was the manual positioning of the micrometer translation stage, because the translation stage micrometer was inside the levitation chamber and opening the cover to the chamber to access the micrometer introduced convection currents. FIG. 3C shows three NaCl particles deposited onto the plate with a center-to-center spacing of 100 µm.

Analytically, these microspot arrays become most useful when the identity of each microspot is known, especially if droplets of different composition were levitated simultaneously. In order to determine how a specific droplet was removed from the EDB over another, experiments were performed to determine if the EDB, because it is a Paul trap, could function as a mass spectrometer and separate particles of different m/z.

Relative Trajectories of Two Levitated Droplets of Different m/z

To achieve this goal, we needed to trap two droplets that were known to have different m/z. The two droplets were generated using an $IP_f$=50 V DC and 100 V DC, which produced a high and a low m/z droplet, respectively. Although we have not directly measured the m/z values of the droplets, it is known that the m/z of the droplet decreases as the $IP_f$ increases. [58]

Figure 4:
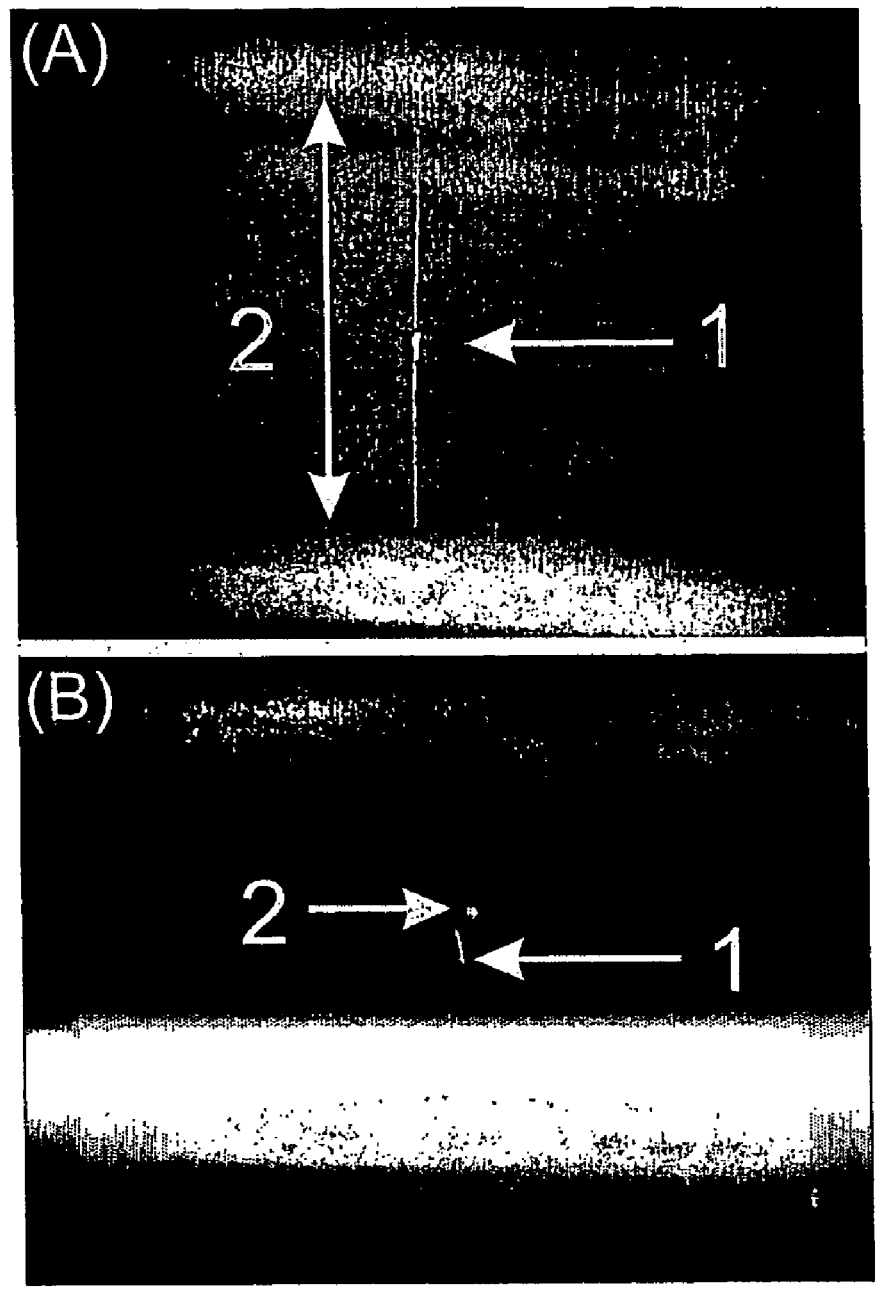
FIG. 4A is a magnified image showing pairs of droplets levitated in the EDB with an applied AC trapping potential of 2500 $V_{0-P}$
FIG. 4B is a magnified image showing pairs of droplets levitated in the EDB with an applied AC trapping potential of 1000 $V_{0-P}$. Droplet (1) was created with a higher m/z relative to droplet (2) by applying an $IP_f$ of 50 V and 100 V, respectively.

FIG. 4A shows the how the relative trajectories of the droplets differ when levitated and how they could be used to identify the relative m/z of the droplets. After the high m/z droplet was levitated, the low m/z droplet was injected into the EDB. Once trapped, the low m/z droplet immediately adopted a trajectory elongated along the z-axis relative to the high m/z droplet. When the AC potential was decreased, the trajectory of the low m/z particle became focused at the null position for the balance, and simultaneously the trajectory of the high m/z particle moved closer to the induction electrode (FIG. 4B). This figure very nicely summarizes the mechanism by which DC fields are used to create a low pass filter on a linear quadrupole, because the AC field cannot correct for the deviation of a high m/z object from the null point by a DC field. [56] Increasing the positive DC potential applied to the MALDI sample plate caused the droplet of highest m/z to be ejected from the balance and deposited, while the lower m/z droplet remained levitated. The lower m/z droplet could itself be deposited by further increasing the potential applied to the MALDI plate.

Microspot Arrays are Ordered from High to Low m/z

Table 1 summarizes the DP for a series of droplet pairs whose relative m/z was varied. Each value in the table is the average of the values measured for five separate pairs of droplets, and the error bars indicate the magnitude of one standard deviation. Table 1 below shows that the pairs of droplets created at identical $IP_f$ (identical m/z) were ejected, within experimental error, from the balance at the same DP.

TABLE 1

| IP$_f$ | | BP | DP | | |
|---|---|---|---|---|---|
| 1$^{st}$ | 2$^{nd}$ | | 1$^{st}$ | 2$^{nd}$ | Difference |
| Identical m/z pairs | | | | | |
| 50$^a$ | 50$^a$ | 53.8 ± 2.4 | 58.6 ± 0.5 | 58.9 ± 0.3 | 0.3 ± 0.6 |
| 100$^a$ | 100$^a$ | 46.3 ± 0.9 | 66.8 ± 1.9 | 69.1 ± 3.5 | 2.3 ± 4.0 |
| 150$^b$ | 150$^b$ | 45.9 ± 1.3 | 91.7 ± 3.0 | 95.8 ± 4.7 | 4.1 ± 4.9 |
| 50$^b$ | 50$^b$ | 57.4 ± 1.5 | 75.2 ± 0.9 | 76.3 ± 1.7 | 1.1 ± 2.3 |
| Different m/z pairs | | | | | |
| 50$^a$ | 100$^a$ | 52.8 ± 1.1 | 61.0 ± 1.0 | 72.0 ± 1.7 | 11 ± 2.0 |
| 50$^b$ | 150$^b$ | 56.6 ± 1.4 | 75.4 ± 1.7 | 99.6 ± 0.7 | 24.2 ± 2.2 |

The amplitude of the AC applied to the levitation ring electrodes was
(a) 1600 V$_{o-p}$ and
(b) 2150 V$_{o-p}$.

Notice that the second droplet deposited always required a slightly higher DP. Again, this can be attributed to space charge, [61-65] and the possible small difference in m/z caused by fluctuations in the experimental parameters governing droplet generation. With droplets created at different IP$_f$ (different m/z), the droplet with the highest m/z was always deposited first. A higher AC trapping potential was required to trap the lower m/z droplets, so the DP of a droplet created with IP$_f$=50 V was lower when trapped with the droplet created with IP$_f$=100V, relative to when it was trapped with the droplet created with IP$_f$=150 V.

The preferential and sequential ejection of the highest m/z droplet upon increase of the DP indicates that the droplets were being separated as a function of m/z by the EDB and hence the EDB was acting as a mass spectrometer for the charged droplets. Therefore the microspot array created on the MALDI plate from a single population of droplets was ordered from high to low m/z. When m/z separation of the particles by deposition from an EDB is combined with MALDI-TOF-MS analysis of the microspots, the overall technique, EDB-MALDI-TOF-MS, can be considered as a novel form of tandem mass spectrometry.[66-67]

Interaction of Adjacent Laser Desorption Plumes of Simultaneously Irradiated Microspots Verified by an Ion-Molecule Reaction The ion-molecule reaction chosen to verify the interaction of adjacent plumes was the gas phase complexation of an alkali metal ion, Cs+, by a linear polyether, poly(ethylene glycol) (PEG). We chose this reaction because it is a well studied system [68-70] and, more importantly, it has been shown that the extent of the cationization of neutral PEG by an alkali metal ion occurring in the desorption plume of a single sample spot peaks at an optimal delayed extraction time. [71] Basically, an increased delayed extraction time allowed for more time for the ion attachment to take place thereby increasing ion signal intensities. Therefore, this was a viable ion-molecule reaction to study because it does occur in the desorption plume. In our study, instead of having the source of both the cations and the neutral polymers being the same desorption plume, we separated the two reactants into two microspots and thus only if their desorption plumes interacted would we see cationization of the neutral PEG by Cs+.

Figure 5:
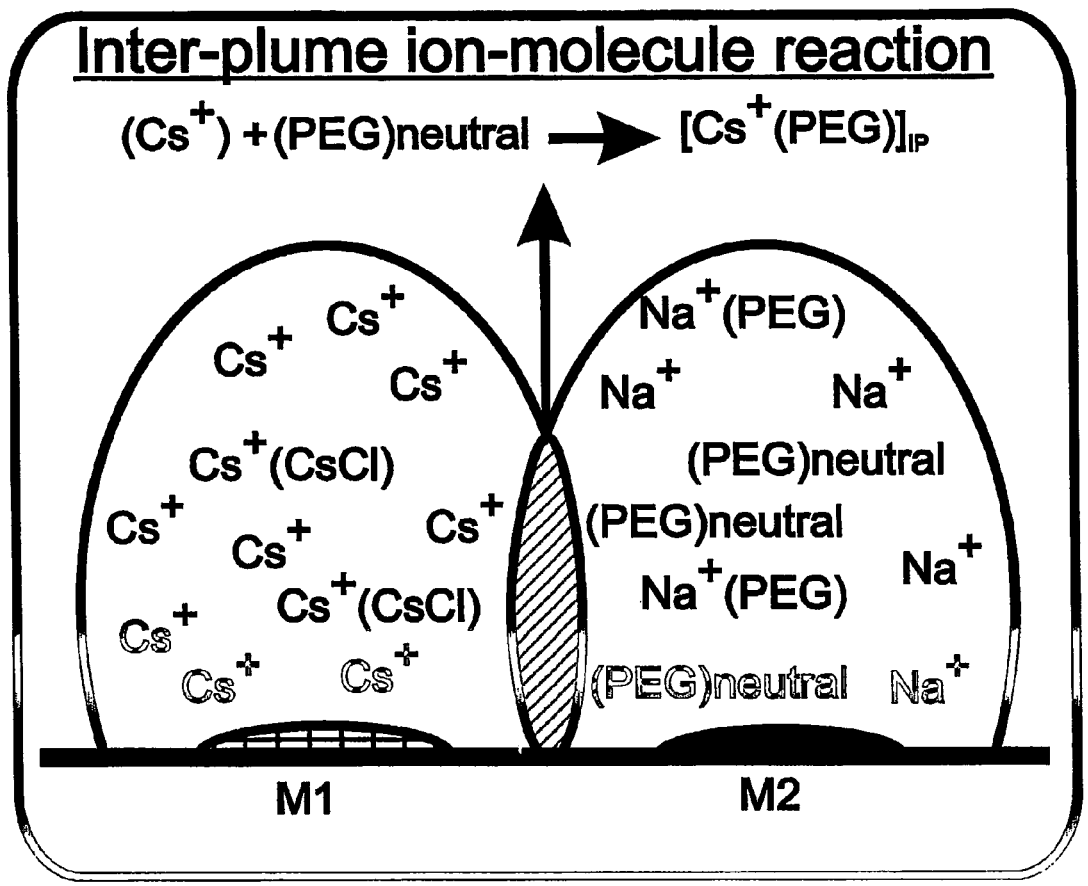
FIG. 5 is a simplified scheme describing the proposed interaction of two laser desorption plumes from adjacent microspots (M1 and M2) and the ion-molecule reaction used to verify the interaction.

FIG. 5 shows a simplified scheme of our interpretation of how the adjacent plumes overlapped to produce an area of interaction where this inter-plume ion-molecule reaction occurred. The depiction of the desorption plumes was based upon a recent imaging study. [72] In this reaction, gas phase cesium ions produced from the first microspot (M1) interacted with neutral PEG ablated from the second microspot (M2), to form cesiated PEG ions, [Cs$^+$(PEG)] in the inter-plume region (IP). In this figure, the high number of Cs$^+$ in the plume of M1 relative to the number of Na$^+$ in M2 was representative of the actual number of moles of Cs$^+$ present in the real microspot M1 relative to the trace levels of Na$^+$ present in M2. Note that because it is a simplification, FIG. 5 also neglects the presence of the MALDI matrix ions and neutrals in either plume.

Figure 6:
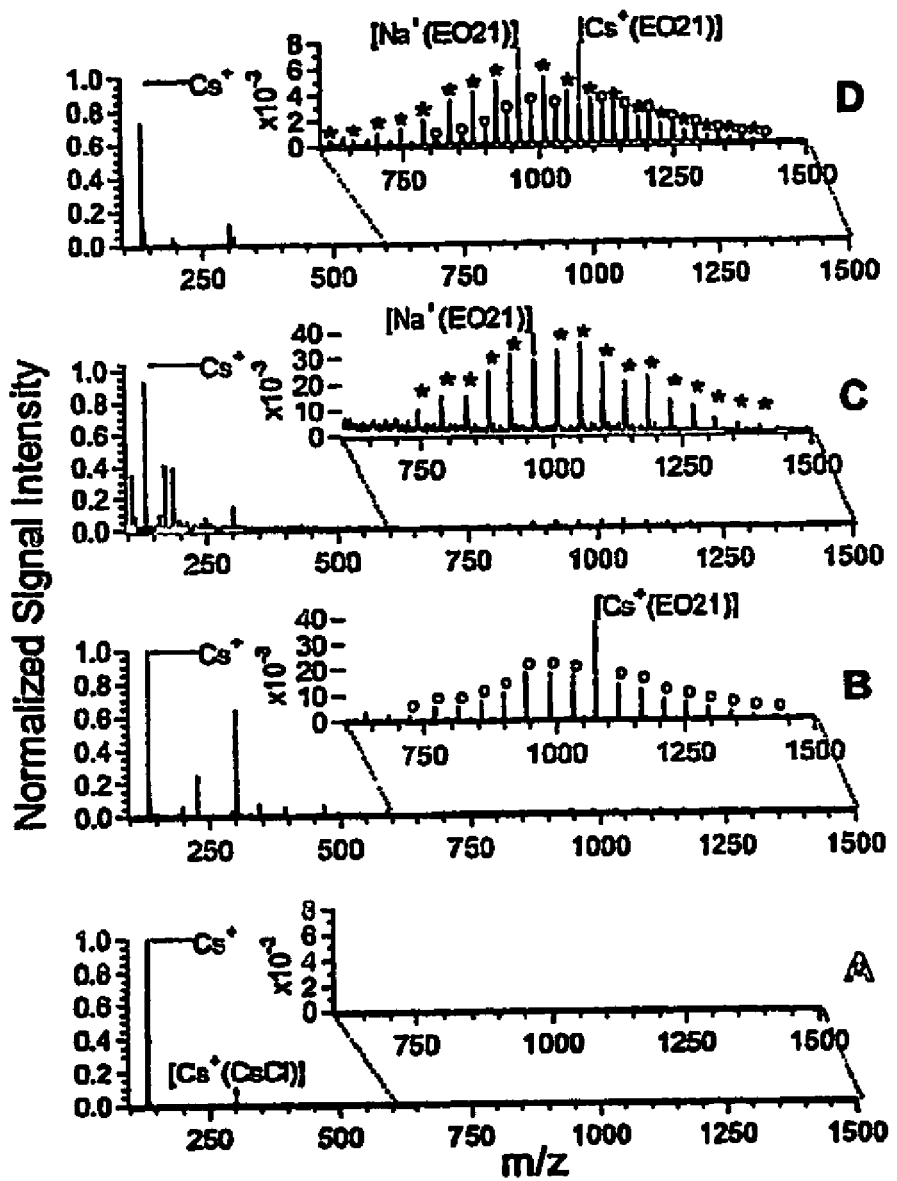
FIG. 6A-6D are a series of mass spectra evidencing interaction between the desorption plumes of two microspots.

FIG. 6 presents the mass spectra that verified the occurrence of an ion-molecule reaction when the desorption plumes of the adjacent microspots interacted. Because both the PEG and CsCl containing microspots were made from levitated particles created using the same droplet generator, a mass spectrum of a pure CsCl microspot only was obtained to verify that no pre-formed [Cs$^+$(PEG)] was present (FIG. 6A). As expected, the only ions observed in this mass spectrum were Cs$^+$ and [Cs$^+$(CsCl)].

A microspot formed by depositing a CsCl containing droplet on top of a PEG containing droplet was analyzed next. This microspot allowed the two components to mix and, because of the high relative concentration of Cs$^+$, all of the PEG was cationized by Cs$^+$ (FIG. 6B). However, when two separate microspots, whose center-to-center spacing was ~115 μm, were analyzed the spectrum observed was simply the sum of the two spectra expected for each microspot analyzed individually (FIG. 6C). Primary matrix ionization using 2,5 dihydroxybenzoic acid has been shown to have a time-scale of about 2 ns, corresponding to a forward expansion of 1-2 μm. [73] However, energy deficit studies and pulsed extraction TOF experiments have suggested that analyte ions may be formed much later, at distances as large as 35 μm. [74-75] Therefore the distance between the two microspots was large enough that no inter-plume interaction could occur, even though both microspots were irradiated simultaneously. The PEG was observed in its sodiated form because of the trace levels sodium present. Note that even though Cs$^+$ is the largest signal in this mass spectrum, there was no cesiated PEG detected.

The analysis of two microspots with a center-to-center spacing of ~84 μm revealed evidence of interaction between the two adjacent desorption plumes. The inset of FIG. 6D shows that upon interaction of adjacent plumes, some neutral PEG molecules coordinated free Cs$^+$ and were thereby detected as [Cs$^+$(PEG)] in the mass spectrum. This inter-plume ion-molecule reaction carries important implications with respect to the ionization mechanism of MALDI because it verifies the existence of gas phase secondary ionization events. Note that it cannot be determined whether the sodiated PEG detected in FIG. 6D was from pre-formed ions in the microspot or from secondary ionization events occurring within its own desorption plume.

This example illustrates that an ensemble of particles levitated in an EDB can be manipulated such that single particles can be ejected into spatially well defined positions onto a MALDI plate to form an array. Because the diameter of the deposited particles is less than that of the laser diameter of the MALDI-TOF-MS, we have developed a rapid means of creating an array of microspots. Simultaneous levitation and subsequent deposition of two particles of different m/z showed that the EDB was capable of functioning as a mass spectrometer for levitated particles by preferentially depositing the highest m/z particle first. Therefore, the particles forming the microspot arrays were ordered from high to low m/z. By simultaneously irradiating adjacent microspots, the interaction of their desorption plumes was detected by the presence of the product of an ion-molecule reaction. Being the first evidence of an inter-plume ion-molecule reaction, this result strongly supports the hypothesis of gas phase secondary ionization events occurring in MALDI.

EXAMPLE 2

Figure 7:
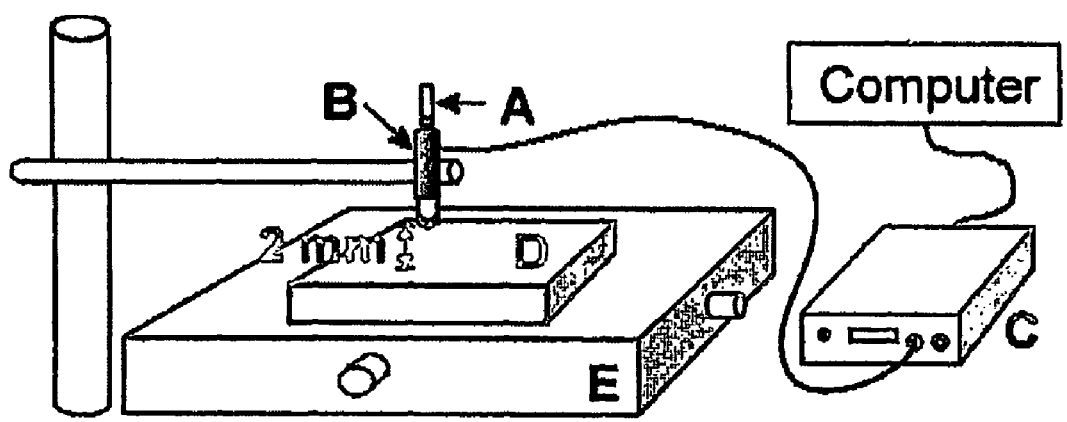
FIG. 7 is a schematic view of an apparatus used to prepare adjacent sample spots. (A) 5 mL solution reservoir, (B) piezoelectric droplet generator, (C) drive electronics, (D) stainless steel MALDI plate, and (E) x-y micrometer translation stage.

A 100 μM solution of angiotension II in water with 0.1% trifluoroacetic acid (TFA) was prepared, and 5 μL of this solution were added to 35 μL of methanol and 10 μL of a 10 mg/mL solution of α-cyano-4-hydroxycinnamic acid (CHCA) to create a 10 μM angiotension II solution. Using a 2-μL pipette, 0.5 μL of this solution was deposited onto a stainless steel MALDI plate and allowed to dry. Next, 10 μL of a 10 μM insulin oxidized chain B solution were prepared in the same proportions as the angiotension II solution and loaded into an ink-jet droplet generator (MJ-AB-01-60; MicroFab Technologies, Inc., Plano, IX, USA) positioned 2 mm above the stainless steel MALDI plate (FIG. 7). Single droplets of ~300 pL were delivered around the periphery of the dried 0.5 μL angiotension II sample spot. Once those spots had dried, a series of adjacent sample spots was created and their digital images were collected (B5; Motic Instruments Inc., Richmond, B.C., Canada) at 10× and 40× magnification (FIG. 8).

Mass spectra from the 0.5 μL sample spot (FIG. 8A) and from one of the 300 pL sample spots around the periphery (FIG. 8B) were collected using a linear mode MALDI-TOF mass spectrometer (Perseptive Biosystems Voyager-DE, Framingham, Mass., USA). After each $5.0 \times 10^2$ mJ laser pulse, a 100 ns delay was implemented before the ions were extracted into the TOF tube. These two mass spectra each displayed ions of a single analyte: angiotension II and insulin oxidized chain B, respectively. By centering the focus of the $N_2$ laser spot (an oval 80×40 μm) between the edges of the two sample spots the simultaneous irradiation of adjacent sample spots was performed. In this case, ions of both analytes were detected (FIG. 8C), producing a mass spectrum that was a composite of the two spectra resulting from analyzing each spot individually.

Figure 8:
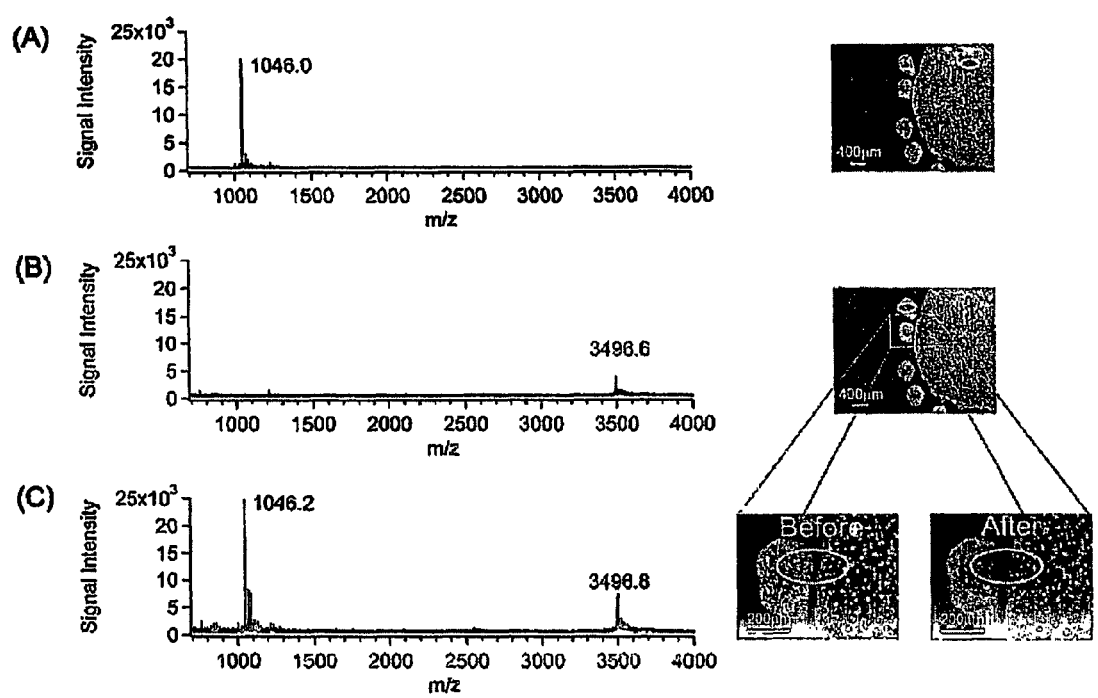
FIG. 8 shows averaged mass spectra of ions produced when the laser was directed and held stationary at (A) a 0.5 mL dried droplet from a solution containing 10 mM angiotension II and 50 mM CHCA, (B) a 300 pL dried droplet containing 10 μM insulin oxidized chain B and 50 mM CHCA, and (C) between the edges of the two adjacent sample spots. Optical microscopy images of the sample spots are included to orient the actual positions of where the laser spot (denoted by the white oval, not to scale) had been directed.

Adjacent to each mass spectrum in FIG. 8 are the images collected before analysis and after 500 laser shots were directed at the sample. The latter image illustrates that material was being ablated/desorbed from both sample spots, supporting the data in the mass spectra. Note that only the first 64 laser shots were averaged to create the mass spectrum shown in FIG. 8C. These data demonstrate that ions created from two discrete sample spots irradiated by a single laser pulse can be analyzed simultaneously. Moskovets et al. rastored the target plate to sequentially laser irradiate two closely spaced sample tracks prepared with a vacuum deposition interface to effect a similar strategy that was shown to improve the accuracy of the mass-to-charge calibration.[13] A different application could be to increase throughput by analyzing two or more samples simultaneously. Such an approach may be useful when positive or negative results are required such as verification of the presence/absence of a specific molecule.

Figure 9:
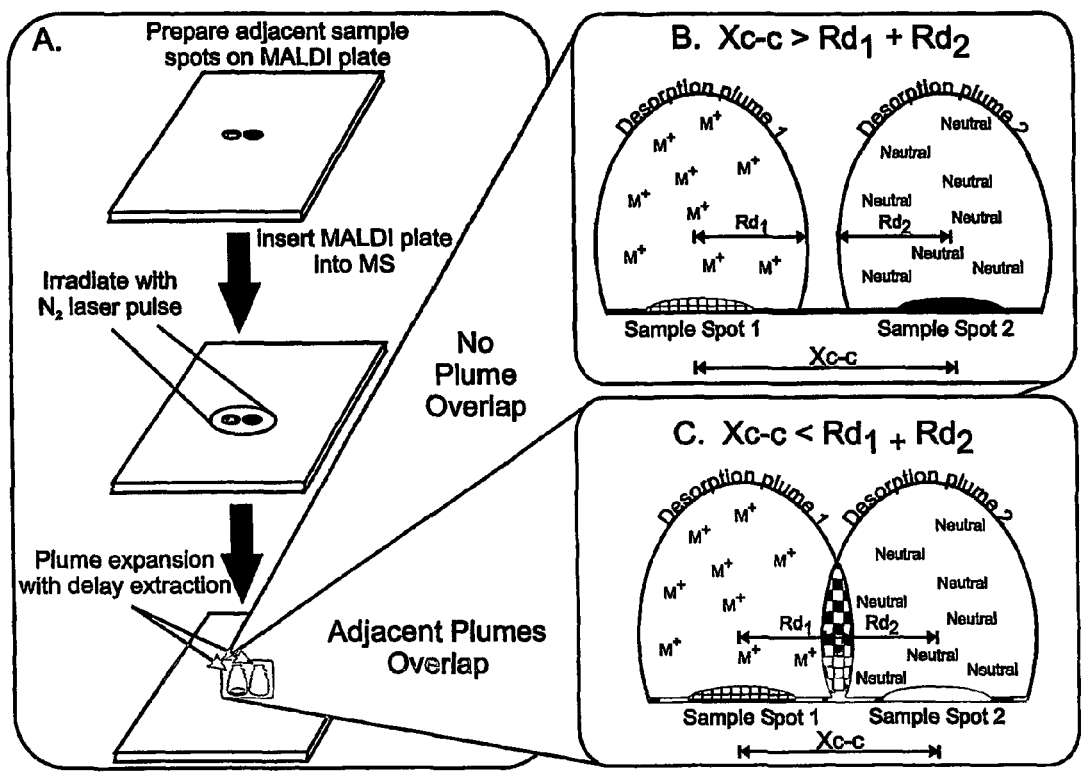
FIG. 9 is schematic view illustrating an inter-plume ion-molecule reaction hypothesis. (A) Artist's rendition of the expanded desorption plumes at a delay time after they were created when two adjacent samples were irradiated simultaneously by a single laser pulse. By considering the center-to-center separation (Xc-c) and the radius of the desorption plumes after a fixed delay time ($Rd_1$ and $Rd_2$ for sample spot 1 and 2, respectively) two different scenarios were derived: Xc-c is sufficiently (B) large that the two plumes do not overlap, or (C) small to facilitate plume overlap.

FIG. 9A illustrates that a third variable must be taken into consideration when analyzing adjacent sample spots in close enough proximity to be irradiated simultaneously with a single laser pulse, namely the radius of each sample spot's desorption plume. This parameter is important when implementing a delay time before extraction of the ions produced after each laser pulse. Matrix molecules expand radially at velocities of the order of 180-330 m/s. [72] If a 100 ns delay was employed before ion extraction, each plume would expand radially a distance of 18-33 mm before the electric field extracted the ions into the field-free region of the TOF. Therefore, if the separation between the edges of the adjacent sample spots is only 20 μm, there is a great potential for the desorption plumes of the two discrete sample spots to overlap. However, if the separation was increased to 200 μm, the extent of plume overlap would be significantly decreased. FIGS. 9B and 9C depict the impact of the proximity of the adjacent spots relative to the radii of their respective desorption plumes (depiction based upon a recent imaging study [72]) upon the interplume overlap.

If such an overlap occurred, it could have an impact on the ions observed in the mass spectrum because the components of each desorption plume include both ions and neutrals, creating potential for gas-phase ion-molecule reactions to occur. For example, the plumes for sample spot 1 and sample spot 2 in both FIGS. 9B and 9C are shown to contain an ion $M^+$ and a neutral molecule, respectively (the MALDI matrix ions and neutrals in both plumes have not been included for simplicity). If the two plumes overlapped, as in FIG. 9B, the gas-phase ion-molecule reaction:

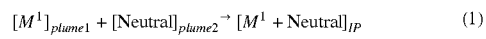

$$[M^1]_{plume1} + [Neutral]_{plume2} \rightarrow [M^1 + Neutral]_{IP} \quad (1)$$

would occur if the neutral molecule has affinity for $M^+$ and the rate of the reaction is sufficiently fast that products are generated during the period of time that the two plumes overlap. If such reactions occurred, the mass spectrum would not be just a composite of the discrete sample spots because of new ions that could not have been created by either of the desorption plumes alone. Consideration of the extent of plume overlap must account for the radial distribution of the components in the plume that are known to vary with the square root of their mass, whereas the axial velocities of the matrix and analyte are essentially identical.[76,77] This means that the heavier analytes tend to be more centrally located and forward peaked whereas the lighter analytes travel further radially.[78]

To test this hypothesis we chose the composition of the two sample spots to mimic the situation described by Eqn. (1). The ion-molecule reaction chosen to verify the interaction of adjacent plumes was the gas-phase complexation of an alkali metal ion by a linear polyether, poly(ethylene glycol) (PEG):

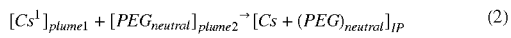

$$[Cs^1]_{plume1} + [PEG_{neutral}]_{plume2} \rightarrow [Cs + (PEG)_{neutral}]_{IP} \quad (2)$$

This reaction was chosen because it has been well studied [68-70] by MALDITOFMS and we have studied it in the past using electrospray ion trap MS. It has been shown that the extent of the cationization of neutral PEG by an alkali metal ion occurring in the desorption plume of a single sample spot peaks at an optimal delayed extraction time because of gas-phase secondary ionization. [71] Therefore, this was a viable ion-molecule reaction to study because it has been shown to occur in the desorption plume of a single sample spot. However, in our study, instead of having the source of both the cations and the neutral polymers being a single desorption plume from a single sample spot, we separated the two reactants into two sample spots that were irradiated simultaneously and thus only if their desorption plumes overlapped would we see cationization of the neutral PEG by Csþ.

The solution used to create the sample spots containing PEG consisted of $5.0 \times 10^{-5}$ M PEG of average molecular weight 1000 u and $1.0 \times 10^{-3}$ M CHCA in a 99:1 methanol/ water solution. The sample spots containing CsCl were made from a solution consisting of $1.0\times10^{-2}$ M CsCl and $1.0\times10^{-3}$ M CHCA in a 99:1 methanol/water solution. The adjacent sample spots were prepared using the procedure described earlier, and, likewise, images were collected before and after analysis (FIG. 10).

Figure 10A:
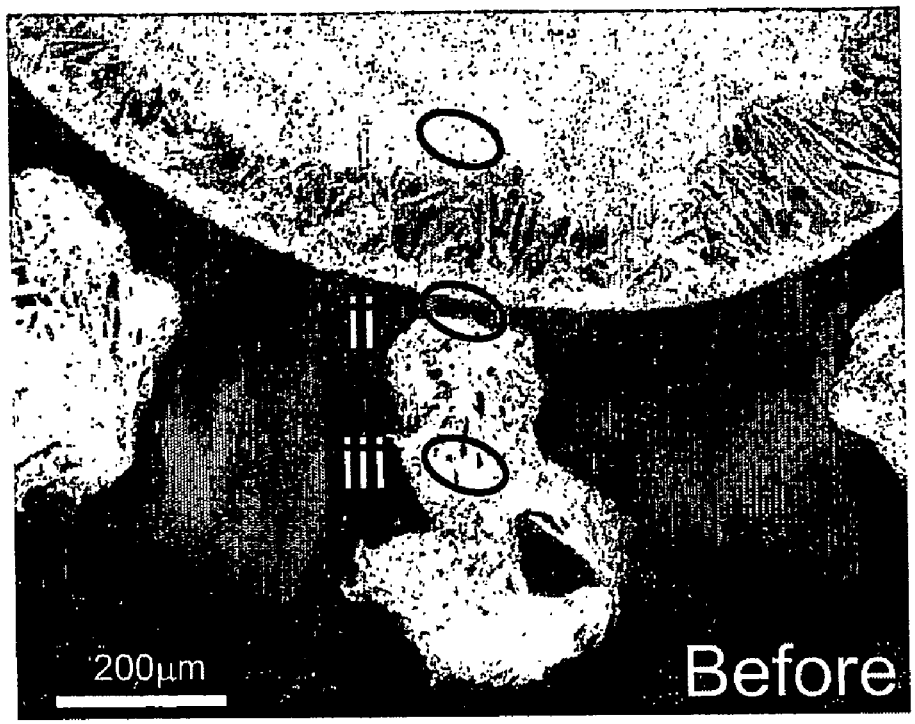
FIGS. 10A and 10B are enlarged images collected (A) before and (B) after mass spectra were collected at positions i, ii, and iii. The black ovals (that are not drawn to scale) approximate the laser spot size at each position.
Figure 10B:
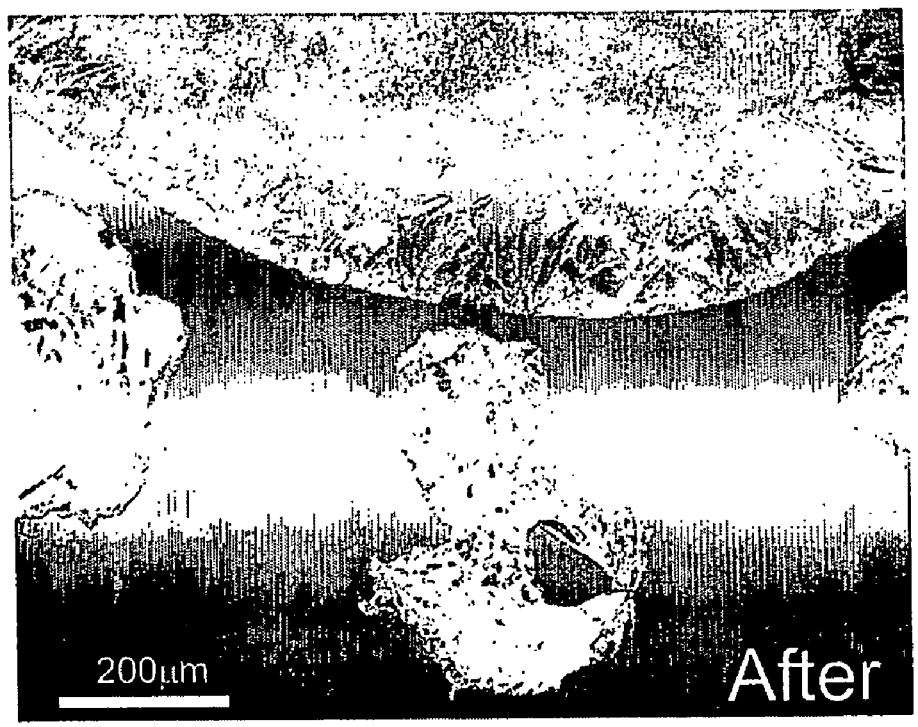
Figure 11:
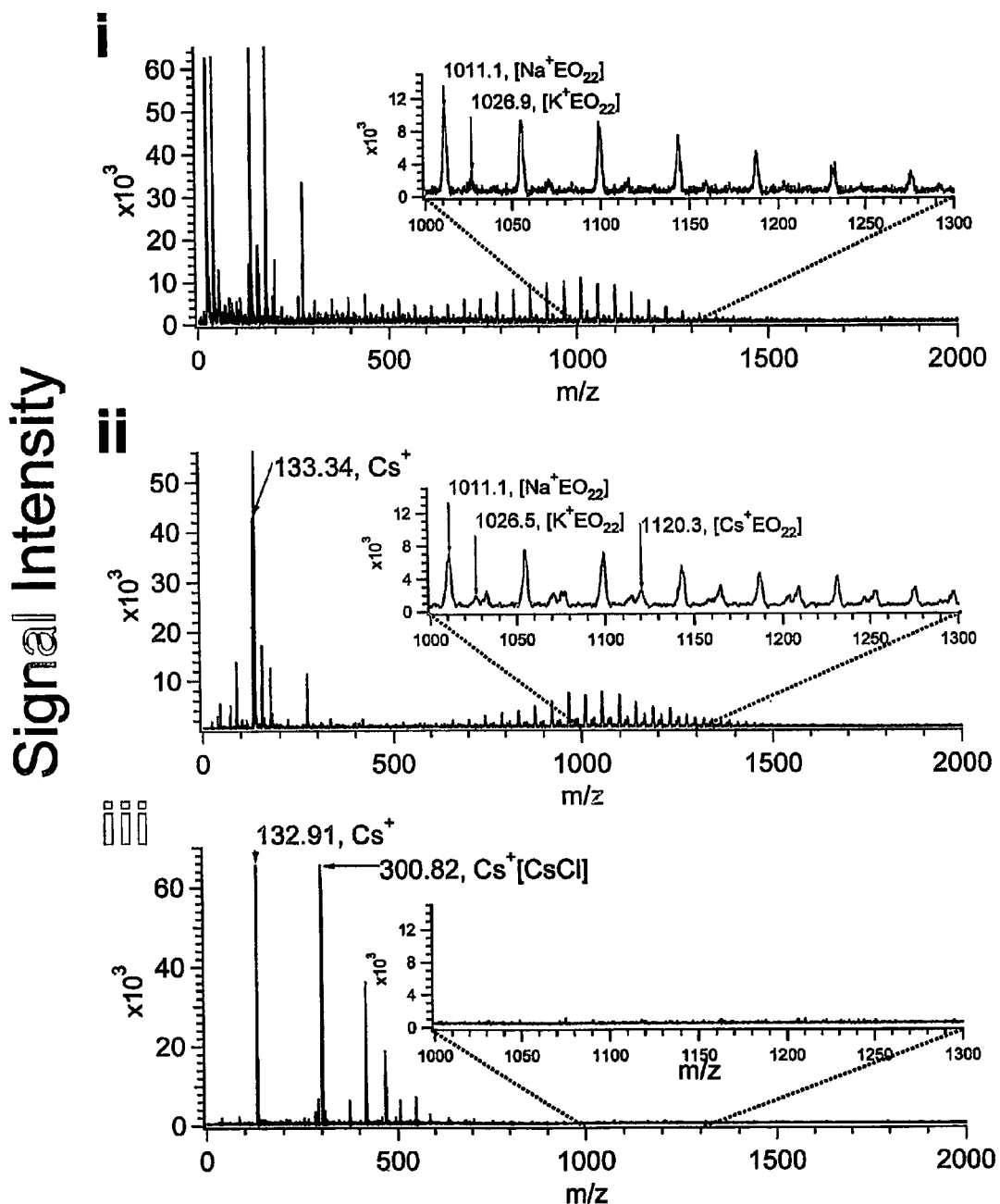
FIG. 11 are averaged mass spectra (16 laser shots) of PEG ions detected at each position in FIG. 10 (i) the PEG/DHB sample; (ii) the simultaneously irradiated samples; and (iii) the CsCl/DHB sample. Each inset show a section of the m/z range that includes the sodiated, potassiated, and cesiated PEG with a degree of polymerization of 22 (EO22).

Mass spectra were collected at the positions indicated as i, ii, and iii in FIG. 10. The black ovals represent the positions where the laser spot was directed to collect each spectrum. By comparing the ions observed in the mass range where the PEG was detected, the overlap of the two desorption plumes was ascertained (FIG. 11). When the sample containing PEG was analyzed (i), the mass spectrum revealed ions corresponding to different degrees of polymerization of PEG that were sodiated. Ions that were potassiated were also observed in small quantities. No sodium or potassium was added to this sample so their source was the solvents, matrix, or PEG itself. The mass spectrum of the CsCl-containing sample spot (iii) showed no ions for PEG, as expected. When the edges of the sample spots, separated by 20 μm, were irradiated simultaneously ions corresponding to sodiated, potassiated, and cesiated PEG were observed. This suggested that the desorption plumes had overlapped and some neutral PEG molecules coordinated free $Cs^+$. Note that because the affinity of PEG for $Cs^+$ is less than that of $Na^+$ and $K^+$ in the gas phase,[79] the $Na^+$ and w $K^+$ were not displaced from the PEG, so any sodiated and potassiated PEG that formed were still detected.

Despite the widespread use of MALDI-TOF-MS over nearly 2.5 decades after it was introduced, there is still debate over the prevailing ionization mechanisms involved. [9,10] For example, it has even been suggested that in some cases secondary reactions in the desorption plume may be so dominant that the primary ionization events may not be reflected at all in the final ion distribution detected in the mass spectrum. [80] To ascertain the dominant physical and chemical mechanisms operating in the MALDI ion source it has been proposed that definitive studies probing the secondary processes occurring in the desorption plume are necessary.[81] The method of simultaneously irradiating adjacent sample spots with a single laser pulse described here will complement the existing techniques used to probe gas-phase ion-molecule reactions in the MALDI ion source, such as the use of delayed extraction,[82] two well-timed single pulses from two lasers [83,85] or two pulses from a single laser. [73,83,86] Overall, it has been demonstrated that by changing the focus from single sample spot analysis by MALDI to the analysis of multiple sample spots simultaneously using a single laser pulse, new avenues of fundamental and applied research can be envisioned.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

1. Tanaka, K.; Waki, H.; Ido, Y.; Akita, S.; Yoshida, Y.; Yohida, T. Protein and polymer analyses up to m/z 100,000 by laser ionization time of flight mass spectrometry Rapid Commun. Mass Spectrom. 1988, 2, 151-153.
2. Karas, M.; Hillenkamp, F. Laser desorption ionization of proteins with molecular masses exceeding 10000 Daltons Anal. Chem. 1988, 60, 2299-2301.
3. Hillenkamp, F.; Karas, M.; Beavis, R.; Chait, B. Matrix Assisted laser desorption/ionization mass spectrometry of biopolymers Anal. Chem. 1991, 63, 1193A.
4. Shevchenko, A.; Sunyaev, S.; Loboda, A.; Shevchenko, A.; Bork, P.; Ens, W.; Standing, K. G. Charting the proteomes of organisms with unsequenced genomes by MALDI-quadrupole time-of-flight mass spectrometry and BLAST homology searching Anal. Chem. 2001, 73, 1917-1926.
5. Shevchenko, A.; Loboda, A.; Shevchenko, A.; Ens, W.; Standing, K. G. MALDI quadrupole time of flight mass spectrometry: A powerful tool for proteomic research Anal. Chem. 2000, 72, 2132-2141.
6. Amiri-Eliasi, B.; Fenselau, C. Characterization of protein biomarkers desrobed by MALDI from whole fungal cells Anal. Chem. 2001, 73, 5228-5231.
7. Berkenkamp, S.; Firpekar, F.; Hillenkamp, F. Infrared MALDI mass spectrometry of large nucleic acids Science 1998, 281, 260-262.
8. Gluckman, M.; Pfenninger, A.; Kruger, R.; Thierolf, M.; Karas, M.; Horneffer, V.; Hillenkamp, F.; Strupat, K. Mechanisms in MALDI analysis: surface interaction or incorporation of analytes Int. J. Mass Spectrom. 2001, 210/211, 121-132.
9. Zenobi, R.; Knochenmuss, R. Ion formation in MALDI mass spectrometry Mass Spectrom. Rev. 1998, 17, 337-366.
10. Knochenmuss, R.; Vertes, A. Time-delayed 2-pulse studeis of MALDI matrix ionization mechanisms J. Phys. Chem. B 2000, 104, 5406-5410.
11. Paul, W. Electromagnetic Traps for Charged and neutral particles Reviews of Modern Physics 1990, 62, 531-540.
12. Smith, J. N.; Flagan, R. C.; Beauchamp, J. L. Droplet evaporation and discharge dynamics in electrospray ionization J. Phys. Chem. A 2002, 106, 9957-9967.
13. Moskovets, E. C., H.-S.; Pashkova, A.; Rejtar, T.; Andreev, V.; Karger, B. L. Closely spaced external standard: a universal method of achieving 5 ppm mass accuracy over the entire MALDI plate in axial matrix-assisted laser desorption/ionization time-of-flight mass spectrometry Rapid Commun. Mass Spectrom. 2003, 17, 2177-2187.
14. Preisler, J.; Hu, P.; Rejtar, T.; Moskovets, E.; Karger, B. L. Capillary array electrophoresis-MALDI mass spectrometry using a vacuum deposition interface Anal. Chem. 2002, 74, 17-25.
15. Rejtar, T.; Hu, P.; Juhasz, P.; Campbell, J. M.; Vestal, M. L.; Preisler, J.; Karger, B. L. Off-line coupling of high-resolution capillary electrophoresis to MALDI-TOF and TOF/TOF MS J. Proteome Res. 2002, 1, 171-179.
16. Keller, B. O.; Li, L. Detection of 25,000 molecules of substance P by MALDI-TOF-MS and investigations into the fundamental limits of detection in MALDI J. Am. Soc. Mass Spectrom. 2001, 12, 1055-1063.
17. Whittal, R. M.; Keller, B. O.; Li, L. Nanoliter chemistry combined with mass spectrometry for peptide mapping of proteins from single mamalian cell lysates Anal. Chem. 1998, 70, 5344-5347.
18. Liu, J.; Tseng, K.; Garcia, B.; Lebrilla, C. B.; Mukerjee, E.; Collins, S.; Smith, R. Electrophoresis separation in open microchannels. A method for coupling electrophoresis with MALDI-MS Anal. Chem. 2001, 73, 2147-2151.
19. Brivio, M.; Fokkens, R. H.; Verboom, W.; Reithoudt, D. N.; Tas, N. R.; Goedbloed, M.; van den Berg, A. Integrated microfluidic system enabling (bio)chemical reactions with on-line MALDI-TOF Mass Spectrometry Anal. Chem. 2002, in press.

20. Onnerfjord, P.; Ekstrom, S.; Bergquist, J.; Nilsson, J.; Laurell, T.; Marko-Varga, G. Rapid Commun. Mass Spectrom. 1999, 13, 315-322.
21. Ekstrom, S.; Onnerfjord, P.; Nilsson, J.; Bengtsson, M.; Laurell, T.; Marko-Varga, G. Anal. Chem. 2000, 72, 286-293.
22. Ekstrom, S.; Ericsson, D.; Onnerfjord, P.; Bengtsson, M.; Nilsson, J.; Marko-Varga, G.; Laurell, T. Anal. Chem. 2001, 73, 214-219.
23. Miliotis, T.; Marko-Varga, G.; Nilsson, J.; Laurell, T. J. Neurosci. Meth. 2001, 109, 41-46.
24. Onnerfjord, P.; Nilsson, J.; Wallman, L.; Laurell, T.; Marko-Varga, G. Anal. Chem. 1998, 70, 4755-4760.
25. Karas M, Hillenkamp F. *Anal. Chem.* 1988; 60: 2299.
26. Karas M, Bahr U, Ingendoh A, Nordhoff E, Stahl B, Strupat K, Hillenkamp F. *Anal. Chim. Acta* 1990; 241: 175.
27. Karas M, Bahr U, Giebmann U. *Mass Spectrom. Rev.* 1992; 10: 335.
28. Murray K. *Mass Spectrom. Rev.* 1997; 16: 283.
29. Wang M Z, Fitzgerald M C. *Anal. Chem.* 2001; 73: 625.
30. Skelton R, Dubois F, Zenobi R. *Anal. Chem* 2000; 72: 1707.
31 Gobom J, Schuerrenberg M, Mueller M, Theiss D, Lehrach H, Nordhoff E. *Anal. Chem.* 2001; 73: 434.
32 Nordhoff E. Schurenberg M, Thiele G, Lubbert C, Kloeppel K-D, Theiss D, Lehrach H, Gobom *J. Int. J. Mass Spectrom.* 2003; 226: 163.
33. Garden R W, Sweedler J V. *Anal. Chem.* 2000; 72: 30.
34. Luxembourg S L, McDonnell L A, Duursma M C, Guo X, Heeren R M A. *Anal. Chem* 2003; 75: 2333.
35. Little D P, Cornish T J, O'Donnel M J, Braun A, Cotter R J, Koster H. *Anal. Chem.* 1997; 69: 4540.
36. Onnerfjord P, Nilsson J, Wallman L, Laurell T, Marko-Varga G. *Anal. Chem.* 1998; 70: 4755.
37. Brivio M, Fokkens R H, Verboom W, Reinhoudt D N, Tas N R Goedbloed M, van den Berg A. *Anal. Chem.* 2002; 74: 3972.
38. Schuerenberg M, Luebbert C, Eickhoff H, Kalkum M. Lehrach H, Nordhoff E. *Anal. Chem.* 2000; 72: 3436.
39. Ekstrom S, Ericsson D, Onnerfjord P, Bengtsson M, Nilsson J, Marko-Varga G, Laurell T. *Anal. Chem.* 2001; 73: 214.
40. Ekstrom S. Onnerfjord P. Nilsson J, Bengtsson M, Laurell T, Marko-Varga G. *Anal. Chem.* 2000; 72: 286.
41. Bogan M J, Agnes G R. *Anal Chem.* 2002; 74: 489.
42. Li L, Golding R F, Whittal R W. *J. Am. Chem. Soc.* 1996; 118: 11662.
43. Keller B O, Li L. *J. Am. Soc. Mass Spectrom.* 2001; 12: 1055.
44. Zhang H, Caprioli R M. *J. Mass Spectrom.* 1996; 31: 1039.
45. Retjar T, Hu P, Juhasz P, Campbell J M, Vestal M L, Preisler J. Karger B L. *J. Proteome Res.* 2002; 1: 171.
46. Preisler J, Hu P, Rejtar T, Moskovets E, Karger B L. *Anal. Chem.* 2002; 74: 17.
47. Rubankhin S S, Garden R W, Fuller R R, Sweedler J V. *Nat. Biotechnol.* 2000; 18: 172.
48. Kruse R, Sweedler J V. *J. Am. Soc. Mass Spectrom.* 2003; 14: 752.
49. Caprioli R M, Farmer T B, Gile *J. Anal. Chem.* 1997; 69: 4751.
50. Chaurand P, Stoeckli M. Caprioli R M. *Anal. Chem.* 1999; 71: 5263.
51. Davis, E. J.; Buehler, M. F.; Ward, T. L. *Rev. Sci. Instrum.* 1990, 61, 1281-1288.
52. Feng, X.; Agnes, G. R. *J. Am. Soc. Mass Spectrom.* 2000, 11, 393-399.
53. Shulman, M. L.; Charlson, R. J.; Davis, E. J. *J. Aerosol Sci.* 1997, 28, 737-752.
54. Wuerker, R. F.; Shelton, H.; Langmuir, R. V. *J. Appl. Phys.* 1959, 30, 342.
55. Dawson, P. H. *Quadrupole Mass Spectrometry and its Applications*; American Institute of Physics: Woodbury, 1995.
56. Miller, P. E.; Denton, M. B. *J. Chem. Educ.* 1986, 63, 617-622.
57. Leary, J. J.; Schmidt, R. L. *J. Chem. Educ.* 1996, 73, 1142-1145.
58. Vehring, R.; Aardahl, C. L.; Davis, E. J.; Schweiger, G.; Covert, D. S. *Rev. Sci. Instru.* 1997, 68, 70-78.
59. Taflin, D. C.; Ward, T. L.; Davis, E. J. *Langmuir* 1989, 5, 376-384.
60. Feng, X.; Bogan, M.; Agnes, G. R. *Anal. Chem.* 2001, 73, 4499-4507.
61. Vedel, F.; Andre, *J. Int. J. Mass Spectrom; Ion Processes* 1985, 65, 1.
62. Ledford, E. B., Jr.; Rempel, D. L.; Gross, M. L. *Anal Chem.* 1984, 56, 2744, 2748.
63. Guan, S. H.; Marshall, A. G. *J. Am. Soc. Mass Spectrom.* 1994, 5, 64-71.
64. Mathurin, J.-C.; Gregoire, S.; Brunot, A.; Tabet, J.-C.; March, R. E.; Catinella, S.; Traldi, P. *J. Mass Spectrom.* 1997, 32, 829-837.
65. Parks, J. H.; Szoke, A. *J. Chem. Phys.* 1995, 103, 1422-1439.
66. Johnson, J. V.; Yost, R. A. *Anal. Chem* 1985, 57, 758A-768A.
67. Porter, C. J.; Beynon, J. H.; Ast, T. *Org. Mass Spectrom.* 1981, 16, 101-114.
68. Wyttenbach, T.; Von Heldon, G.; Bowers, M. T. *Int. J. Mass Spectrom. Ion Processes* 1997, 165/166, 377-390.
69. Gidden, J.; Wyttenbach, T.; Jackson, A. T.; Scrivens, J. H.; Bowers, M. T. *J. Am. Soc. Chem.* 2000, 122, 4692-4699.
70. Rashidzadeh, H.; Wang, Y.; Guo, B. *Rapid Communications in Mass Spectrometry* 2000, 14, 439-443.
71. Mowat, I. A.; Donovan, R. J.; Maier, R. J. *Rapid Communications in Mass Spectrometry* 1997, 11, 89-98.
72. Puretzky, A. A.; Geohegan, D. B.; Hurst, G. B.; Buchanan, M. V. *Phys. Rev. Lett.* 1999, 83, 444-447.
73. Knochenmuss, R.; Vertes, A. *J. Phys. Chem. B* 2000, 104, 5406-5410.
74. Zhou, J.; Ens, Standing, K. G.; Verentchikov, A. *Rapid Commun. Mass Spectrom* 1992, 6, 671-678.
75. Kinsel, G. R.; Gimon-Kinsel, M. E.; Gillig, K. J.; Russell, D. H. *Journal of Mass Spectrometry* 1999, 34, 684-690.
76. Zhigilei L V, Kodali P B S, Garrison B J. *J. Phys. Chem. B* 1998; 102: 2845.
77. Zhigilei L V, Garrison B J. *Rapid Commun. Mass Spectrom.* 1998; 12: 1273.
78. Zhang W, Chait B T. *Int. J. Mass Spectrom.* 1997; 160: 259.
79. Bogan M J, Agnes G R. *J. Am. Soc. Mass Spectrom.* 2002; 13: 177.
80. Knochenmuss R, Stortelder A, Breuker K, Zenobi R. *J. Mass Spectrom.* 2000; 35: 1237.
81. Papantonakis M R, Kim J. Hess W P, Haglund R F Jr. *J. Mass Spectrom.* 2002; 37: 639.
82. Wang B H, Dreisewerd K. Bahr U, Karas M, Hillenkamp F. *J. Am. Soc. Mass Spectrom.* 1993; 4: 393.
83. Dreisewerd K. *Chem. Rev.* 2003; 103: 395.
84. Belov M E, Myatt C P, Derrick P *J. Chem. Phys. Lett.* 1988; 284: 412.
85. Little M W, Kim J-K, Murray K. *J. Mass Spectrom.* 2003; 38: 772.
86. Knochenmuss R. *Anal. Chem.* 2003; 75: 2199.

What is claimed is:

1. A method of mass spectrometric analysis of a sample material comprising:
   (a) providing a laser with a laser beam of a defined diameter;
   (b) controllably forming two or more discrete microspots on a substrate in close proximity to one another such that at least part of said two or more discrete microspots fits within said diameter of said laser beam, and wherein at least one of said microspots comprises said sample material;
   (c) irradiating said microspots with said laser beam simultaneously, and
   (d) detecting ions produced by irradiation of said microspots by mass spectrometry.

2. The method as defined in claim 1, wherein said irradiating causes the desorption plumes of said microspots to interact in a gas phase.

3. The method as defined in claim 2, wherein said desorption plumes interact by ion-molecule reactions.

4. The method as defined in claim 3, further comprising detecting secondary ionization in said gas phase.

5. The method as defined in claim 1, wherein said mass spectrometry is time of flight mass spectrometry.

6. The method as defined in claim 1, wherein said microspots are formed on said substrate in a predetermined array or pattern.

7. The method as defined in claim 1, wherein the diameter of each of said microspots is within the range of approximately 1 to approximately 200 μm.

8. The method as defined in claim 7, wherein the diameter of each of said microspots is less than about 100 μm.

9. The method as defined in claim 1, wherein the distance between at least two of said microspots is less than the focused output of a single laser.

10. The method as defined in claim 9 wherein said distance is less than about 200 μm.

11. The method as defined in claim 1, wherein said forming comprises moving said sample material from an electrodynamic balance to said substrate.

12. The method as defined in claim 1, wherein said forming comprises forming said microspots on said substrate using a micropipette.

13. The method as defined in claim 1, wherein said forming comprises forming said microspots on said substrate using an ink-jet droplet generator.

14. The method as defined in claim 1, wherein at least one of said microspots comprises a calibrant having known mass.

15. The method as defined in claim 14, wherein said calibrant is mixed with said sample material in at least one of said microspots.

16. The method as defined in claim 15, wherein said calibrant is deposited in a microspot separate from at least one of said microspots containing said sample material.

17. The method as defined in claim 1, wherein a plurality of said microspots are formed in close proximity in a test region of said substrate, wherein a first one of said microspots comprises said sample material mixed with a first amount of matrix material and a second one of said microspots comprises said sample material mixed with a second amount of said matrix material, wherein said first and second amounts differ.

18. The method as defined in claim 1, wherein a plurality of said microspots are formed in close proximity in a test region of said substrate, wherein a first one of said microspots comprises said sample material mixed with a first matrix material and a second one of said microspots comprises said sample material mixed with a second matrix material, wherein said first and second matrix materials differ.

19. The method as defined in claim 18, wherein said test region is smaller in size than the focused output of a single laser, and wherein at least said first and second ones of said microspots are irradiated simultaneously.

20. The method as defined in claim 19, wherein at least one of said first and second matrix materials comprise a mixture of different matrices.

21. The method as defined in claim 20, wherein at least some of said microspots formed within said test region comprise materials selected to improve the ionization yield of said sample material in a gas phase.

22. The method as defined in claim 20, wherein at least some of said microspots formed within said test region comprise materials selected to increase the frequency of ion-molecule collisions in said a gas phase.

23. The method as defined in claim 1, wherein said irradiating comprises directing single or multiple laser shots to said microspots.

24. The method as defined in claim 1, wherein said sample material is a mixture of different types of compounds.

25. The method as defined in claim 1, wherein said sample material comprises a biomolecule.

26. The method as defined in claim 1, wherein an array of microspots of known composition are formed on said substrate, wherein said microspots comprise different sample materials.

27. The method as defined in claim 1, wherein a test region of said substrate comprises a test material, and wherein said microspots are formed in said test region.

28. The method as defined in claim 27, wherein at least some of said microspots comprise sample material potentially reactive with said test material.

29. The method as defined in claim 28, wherein said sample material comprises at least one known chemical reagent.

30. The method as defined in claim 1, wherein said sample material comprises an analyte deposited on said substrate in a form selected from the group consisting of a solid member, a droplet, a single molecule or a cluster of molecules.

31. The method as defined in claim 1, wherein said microspots are controllably formed on said substrate by sequentially removing charged particles from an electrodynamic balance to said substrate, wherein said charged particles are deposited on said substrate in an array corresponding to the mass-to-charge ratios of said particles.

32. The method as defined in claim 1, wherein said substrate comprises a test region having at least one microfabricated pattern formed therein.

33. The method as defined in claim 32, wherein said microfabricated pattern defines reservoirs for holding materials selected from the group consisting of a reagents, calibrants, solvents, gas phase ionization yield enhancers and said sample material.

34. The method as defined in claim 32, wherein as least some of said reservoirs are in fluid communication.

35. The method as defined in claim 1, wherein said controllably forming comprises electrodynamically depositing discrete droplets on said substrate at the location of said microspots.

36. The method as defined in claim 35, wherein said electrodynamically depositing comprises controllably moving each of said droplets from an electrodynamic balance to said substrate.

37. A method of mass spectrometric analysis of a sample material comprising:
(a) providing a laser with a laser beam of a defined diameter;
(b) controllably forming two or more discrete microspots on a substrate in close proximity to one another such that at least part of said two or more discrete microspots fits within said diameter of said laser beam, and wherein at least one of said microspots comprises said sample material;
(c) irradiating said microspots with said laser beam simultaneously, wherein said irradiating causes the desorption plumes of said microspots to interact in a gas phase, and
(d) detecting ions produced by interaction of said desorption plumes by mass spectrometry.

38. The method as defined in claim 37, wherein the interaction of said desorption plumes comprises ion-molecule reactions.

* * * * *